United States Patent [19]

Giacobbe et al.

[11] Patent Number: 5,112,519
[45] Date of Patent: May 12, 1992

[54] PROCESS FOR PRODUCTION OF BIODEGRADABLE SURFACTANTS AND COMPOSITIONS THEREOF

[75] Inventors: Thomas J. Giacobbe, Skillman; George A. Ksenic, Edison, both of N.J.

[73] Assignee: Mobil Oil Corporation, Fairfax, Va.

[21] Appl. No.: 361,628

[22] Filed: Jun. 5, 1989

[51] Int. Cl.$^5$ ................................................ C11D 1/66
[52] U.S. Cl. .................... 252/174.21; 252/DIG. 2; 568/618; 568/671; 568/909; 585/533; 585/651
[58] Field of Search ................ 568/618, 671, 909; 252/174.21, DIG. 2; 585/533, 651

[56] References Cited

U.S. PATENT DOCUMENTS

| | | | |
|---|---|---|---|
| 2,870,220 | 1/1959 | Carter | 568/618 |
| 3,053,903 | 9/1962 | Holland | 568/615 |
| 3,239,566 | 3/1966 | Slaugh et al. | |
| 3,239,569 | 3/1966 | Slaugh et al. | |
| 3,239,570 | 3/1966 | Slaugh et al. | |
| 3,400,163 | 9/1968 | Mason et al. | |
| 3,420,898 | 1/1969 | Van Winkle et al. | |
| 3,440,291 | 4/1969 | Van Winkle et al. | |
| 3,496,203 | 2/1970 | Morris et al. | |
| 3,496,204 | 2/1970 | Morris et al. | |
| 3,502,730 | 3/1970 | Mason et al. | |
| 3,527,818 | 9/1970 | Mason et al. | |
| 3,792,106 | 2/1974 | Regier | 585/651 |
| 4,104,151 | 8/1978 | Rubin et al. | 208/111 |
| 4,400,561 | 8/1983 | Mitchell et al. | 585/435 |
| 4,855,527 | 8/1989 | Page et al. | 585/527 |
| 4,982,031 | 1/1991 | Chen | 585/624 |

OTHER PUBLICATIONS

*Hydroformylation with Cobalt Carbonyl and Cobalt Carbonyl-Tributylphosphine Catalysts*, M. Van Boven et al., Laboratory for Chemical Technology, Twenti University of Technology, The Netherlands.
*Monolydric Alcohols, Manufacture, Applications, and Chemistry*, Wickson, Exxon Chemical Company.
Polyoxyethylation of Alcohol, Ind. Eng. Chem., 49(11), 1875-1878 (1957).
Conversion of Neodol Alcohols and Ethoxylates To Anionic Surfactants By Sulfation, Technical Bulletin--Shell Chemical Company, SC:372-380.
Aliphatic Compounds, Practical Organic Chemistry, Arthur Vogel, 3rd Edition, p. 303 (1956).
A Low-Pressure System for Producing Normal Aldehydes By Hydroformylation of Alpha-Olefins, Pruett et al., J. Org. Chem., vol. 34, No. 2, pp. 327-330 (1968).
Hydroformylating Terminal Olefins, Ind. Chem. Prod. Res. Develop, 9(4), 516-520 (1970).
Neodol 25, Technical Bulletin Shell Chemical Company, SC:84-86.
Synthetic Detergents, A. Davidsohn et al., 6th Edition, pp. 38-68 (1978).
Surfactants and Detersive Systems, vol. 22, pp. 360-363.
Neodol Formulary, pp. 27-34.
Detergent Alcohols-Synthetic vs. Natural, Soap/Cosmetics/Chemical Specialties for Mar. 1989, pp. 26, 28-30, 32, 80-81.

(List continued on next page.)

Primary Examiner—Paul Lieberman
Assistant Examiner—Bradley A. Swope
Attorney, Agent, or Firm—Alexander J. McKillop; Charles J. Speciale; L. G. Wise

[57] ABSTRACT

This invention relates to processes for making biodegradable surfactant. The process comprises several steps including an optional step. The first step is directed to reacting olefins with ZSM-23 catalyst to form oligomers having the formula $(C_3)_x$, $(C_4)_x$ or mixtures thereof. Second, the oligomer is hydroformylated to form a saturated alcohol, for example, tridecanol. Next, the saturated alcohol is ethoxylated. Thereafter a nonionic biodegradable surfactant is recovered. This surfactant can be used in detergent formulations. A process is also taught for making esters which can be used as lubricants or plasticizers. A specific hydroformylation process is taught which utilizes modified cobalt carbonyl catalyst. Also, a specific ethoxylation process is taught. Products formed according to the latter two processes as well as their uses are also taught.

8 Claims, 4 Drawing Sheets

OTHER PUBLICATIONS

New Syntheses With Carbon Monoxide, New York, 1980.

Monohydric Alcohols, ACS Symposium, Series 159, Wash., D.C. (1981).

Catalytic Activation of Carbon Monoxide, ACS Symposium, Series 152, Washington, D.C. (1981).

Novel Hydroformylation Catalysts, J. Organomet. Chem., 13, 469–477 (1968).

Hydroformylation of 1-Olefins in Tertiary Organophosphine-Cobalt Hydrocarbonyl Catalyst Systems, I & EC Prod Res. & Dev., 8(2), 214 (1969).

Stereochemistry of the Hydroformylation of Olefinic Hydrocarbons With Cobalt and Rhodium Catalyst, J. Amer. Chem. Soc. 99(4), 1058–1063 (1977).

Hydroformylation With Cobalt Carbonyl and Cobalt Carbonyl-Tributylphosphine Catalysts, Ind. Eng. Chem. Prod. Res. Develop. 14(4), 259–264 (1975).

In Situ Infrared Spectral Studies On The Cobalt Carbonyl-Catalyzed Hydroformylation of Olefins, J. Organometallic Chem. 66, C23–C25 (1974).

Photochemical Ligand Dissociation, Electron Transfer & Metal-Metal Bond Cleavage of Phosphine-Substituted Cobalt Carbonyl Complexes, Organometallics, 3, 900–903 (1984).

Microcrystalline Waxes, 1. Investigations on the Structure Of Waxes By Proton Nuclear Magnetic Resonance Spectrospocy, Chem. Tech. Biotechnol. 31, 693 (1981).

Infrared Spectra of Some Derivatives of Octacarbonyldecobalt, J. Chem. Soc. (A), 1135–1137 (1968).

Kinetics and Mechanisms of Substitution Reactions of Dicobalt Octacarbonyl; Ph.D. Dissertation, University of Illinois, 22–32 (1980).

The Preparation of Organo-Phosphines by the Addition of Phosphine to Unsaturated Compounds, J. Amer. Chem. Soc., 74, 3282–3284 (1952).

The Free Radical Addition of Phosphines to Unsaturated Compounds, J. Org. Chem. 26, 5138–5145 (1961).

Steric Effects of Phosphorus Ligands in Organometallic Chemistry and Homogeneous Catalysts, Chem. Reviews 77(3), 313–348 (1977).

A Low-Pressure System for Producing Normal Aldehydes By Hydroformylation of Alpha-Olefins, J. Org. Chem. 34(2), 327–330 (1969).

Gas-Liquid Chromatographic Separation of Ethylene Oxide Adducts of Fatty Alcohols Via Their Acetate Esters, J. Amer. Oil Chem. Soc., 42, 69–71 (1965).

Separation by Gas Chromatography of Alcohol-Ethylene Oxide Adducts, Acta Chem. Scandivanica, 20, 572–573 (1966).

Ethylene Oxide Oligomers Distribution Nonionic Surfactants Via High Performance Liquid Chromatography, J. Amer. Oil Chem. Soc., 58(10), 950–957 (1981).

Determination of Ethylene Oxide Oligomer Distribution in Alcohol Ethoxylates by HPLC Using A Rotating Disc-Flame Ionization Detector, AOSC Meeting, New Orleans, May 1981; Shell Chemical Co. Technical Bulletin, SC:580.82.

Monohydric Alcohols, ACS Symposium, Series 159, Amer. Chem. Soc., Washington, D.C. 101–112 (1981).

FIG. 2
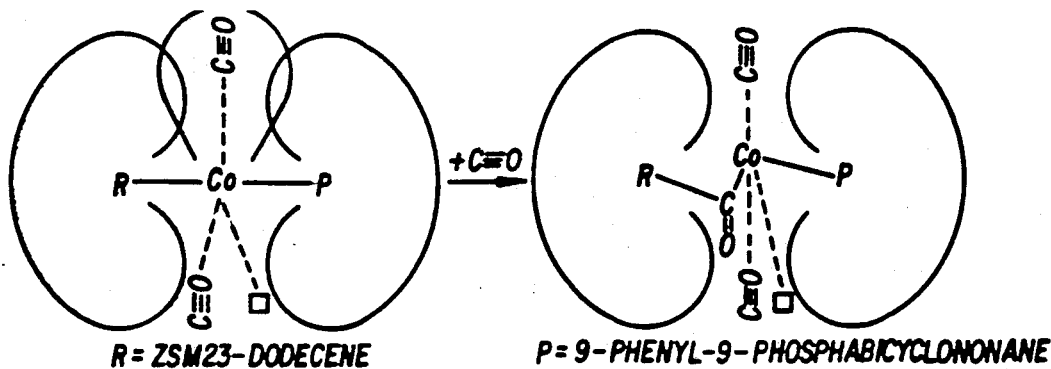
R = ZSM23-DODECENE    P = 9-PHENYL-9-PHOSPHABICYCLONONANE
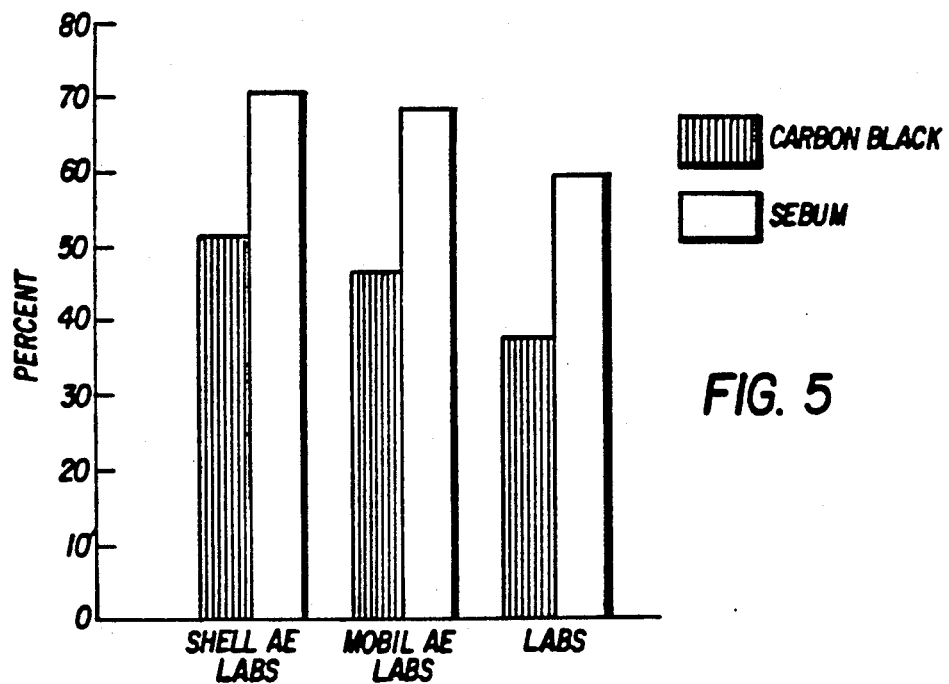
FIG. 5
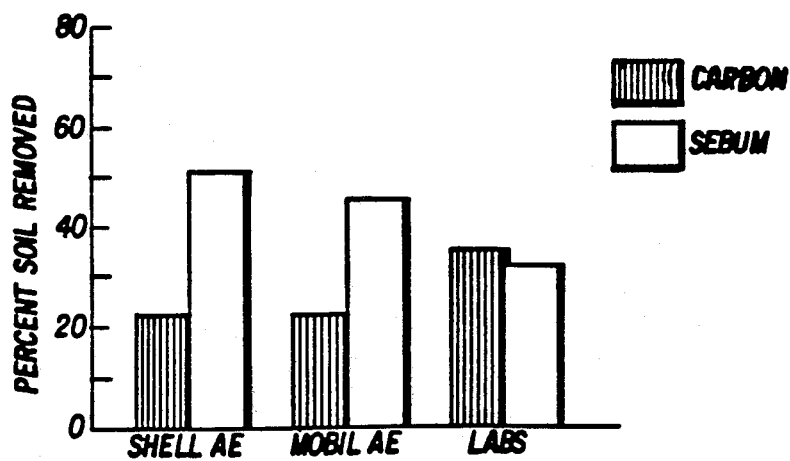
FIG. 6

PROCESS FOR PRODUCTION OF BIODEGRADABLE SURFACTANTS AND COMPOSITIONS THEREOF

FIELD OF THE INVENTION

The invention relates to a process for preparing surfactants and processes for preparing intermediates used in forming those surfactants. Specifically, the invention relates to the formation of tridecanol, nonionic tridecanol-ethoxylates and anionic tridecanol-ethoxylate sulphates. The invention relates to products formed from the processes as well as uses for the intermediates and surfactant products. The latter product can be used in detergent formulations.

BACKGROUND OF THE INVENTION

Detergents typically contain surfactant and builder. A high performance builder may contain phosphate, silicate, alkali and antiredeposition agent. See A. Davidsohn, *Synthetic Detergents*, 7th Edition, Chapter 3, John Wiley & Sons, New York (1987). Builders extend or enhance the surfactant. They soften the water by sequestering calcium and magnesium ions. They inhibit metal corrosion. They make the wash water basic for saponifying glycerides and prevent liberated soil from redepositing on fabric.

Commercially, anionic and nonionic surfactants are most important. Anionic linear alkylbenzene sulfonates (LABS) dominate anionic surfactants. Alcohol-ethoxylates (AE) dominate nonionic surfactants. They have a growing market share. Growth comes from decreasing phosphate use and their superior performance. Phosphate bans, a growing political reality, cause manufacturers to use more surfactant to soften wash water. Moreover, alcohol-ethoxylates remove more sebaceous soil than do linear alkylbenzene sulfonates. The also perform better in both hard and cold water. They formulate more easily into liquid detergents.

Commerical standards have evolved. Dodecylbenzenesulfonic acid sodium salt by Vista Chemical Company and $C_{12-15}$ alcohol 9-mole-ethoxylate by Shell Chemical Company are among those standards. Manufacture of dodecylbenzenesulfonic acid sodium salt is well documented. Davidsohn, A. S., Milwidsky, B., *Synthetic Detergents*, 7th Rd., John Wiley, N.Y., 124-127 (1987), hereby incorporated by reference.

NEODOL 25 is a $C_{12-15}$ linear primary alcohol. See Technical Bulletin SC:84-86 by the Shell Chemical Company. This alcohol is made by a manufacturing process developed by Shell. Surfactants are made from this product. See U.S. Pat. Nos. 3,496,204 and 3,496,203 concerning tertiary organophosphine-cobalt-carbonyl complexes utilized in hydroformulation processes to effect reaction products consisting predominately of primary alcohol by reacting an olefin compound with carbon monoxide in hydrogen at a temperature between about 100° and 300° C. in the presence of the complex. See also U.S. Pat. Nos. 3,440,291; 3,420,898; 3,239,570; 3,239,569; 3,239,566 regarding hydroformylation of olefins. NEODOL 25 has low toxicity. But, undiluted alcohol can be severely irritating to the eye, and on repeated or prolonged dermal contact may be irritating to the skin.

Conventional surfactant synthesis such as that utilized by Shell involves alpha olefin formation based on ethylene as a reactant so that an olefin is formed of the formula $(C_2)_x$. That alpha olefin or its internal double bond isomer is subjected to hydroformylation, that is, reaction in the presence of carbon monoxide in hydrogen utilizing a specific catalyst to form an alcohol. That alcohol is ethoxylated in a conventional manner to form an alcohol-ethoxylate. Thereafter, that compound is sulfonated to form an alcohol-ethoxysulphate. Shell utilizes a catalyst of cobalt in a complex combination with carbon monoxide and a tertiary six-membered heterocyclic phosphine.

EXXAL 13 is a highly methyl-branched tridecylalcohol known for its use in lubricants and detergent formulations which does not require rapid biodegradation.

Applicants have discovered a biodegradable surfactant equal to the commercial surfactants used above. However, applicants' surfactant provides superior economic advantages as well as safety advantages compared to the commercial products.

SUMMARY OF THE INVENTION

The invention relates to a process for making biodegradable surfactant comprising a) reacting olefins with ZSM-23 catalyst to form oligomers having the formula $(C_3)_x$, $(C_4)_x$ or mixtures thereof where x has the value of 1 to 10; b) hydroformylating the oligomer to form a saturated alcohol; c) ethoxylating the saturated alcohol; and d) recovering a nonionic biodegradable surfactant.

The invention further relates to a detergent comprising a surfactant selected from a nonionic $C_{10}$–$C_{16}$ alcohol-ethoxylate or an anionic $C_{10}$–$C_{16}$ alcohol-ethoxylate sulphate or alcohol sulfate and salts thereof as well as mixtures thereof.

The invention also relates to a process for making esters comprising reacting olefins with ZSM-23 catalyst to form oligomers having the formula $(C_3)_x$ or $(C_4)_x$ or mixtures thereof, where x has the value of 1 to 10, hydroformylating the oligomer and recovering a semi-linear alcohol having less than 1.4 methyl branches whereby the recovered ester has improved low temperature properties, decreased volatility and higher viscosity index compared to isotridecyl alcohol.

The invention relates to a lubricant or plasticizer product comprising a semi-linear alcohol having less than 1.4 methyl branches, having improved low temperature properties, decreased volatility and higher viscosity index compared to isotridecyl alcohol.

The invention further relates to a process for hydroformulation comprising reacting olefins having the formula $(C_3)_x$, $(C_4)_x$ or mixtures thereof, where x has the value of 1 to 10, with a phosphine ligand at a temperature sufficient to promote reaction while retarding paraffin formation.

The invention further relates to a process for preparing nonionic tridecanol-ethoxylate comprising reacting tridecanol with ethylene oxide in the presence of a potassium alcoholate catalyst.

The invention further relates to a nonionic $C_{10}$–$C_{16}$ alcohol-ethoxylate.

The invention relates to a surfactant comprising a nonionic $C_{10}$–$C_{16}$ alcohol-ethoxylate.

The invention further relates to an anionic $C_{10}$–$C_{16}$ alcohol ethoxylate sulphate and salts thereof.

The invention relates to a surfactant comprising an anionic $C_{10}$–$C_{16}$ alcohol ethoxylate sulphate and salts thereof.

BRIEF DESCRIPTION OF THE DRAWINGS

The invention is described using the following figures which are not intended to limit the invention.

FIG. 2 shows promotion of CO insertion and alcohol synthesis;

FIG. 5 summarizes soil removal data for phosphorous built liquid;

FIG. 6 summarizes soil removal data for unbuilt liquid;

DETAILED DESCRIPTION OF THE INVENTION

Figure 1:
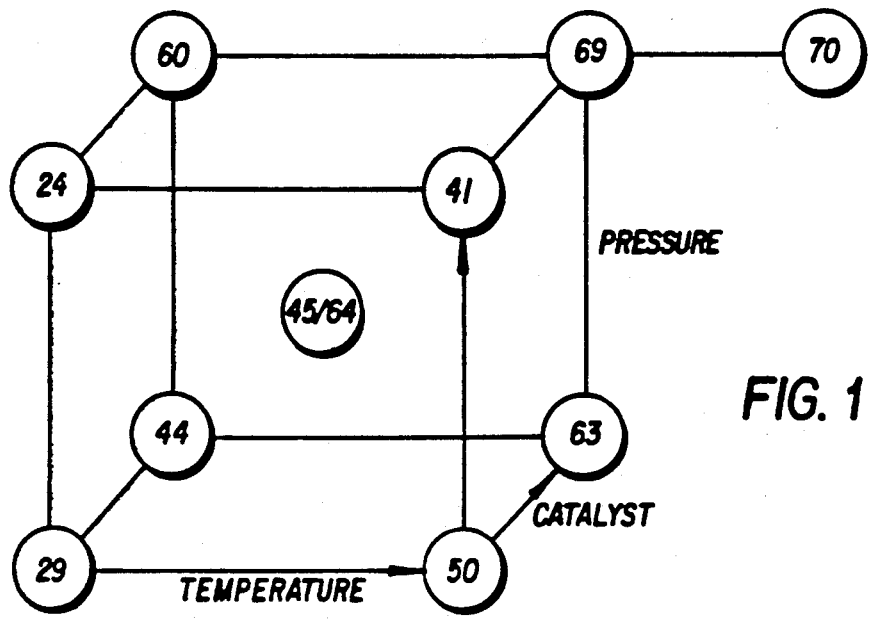
FIG. 1 shows yields for tridecanol preparation by hydroformylation with ZSM23-dodecenes.

This invention relates to a process for making biodegradable surfactants for use in detergent formulations. Several steps are required to make the surfactant as well as an optional step. The first step involves reacting olefins with a zeolite catalyst to form oligomers. The second step involves hydroformylating the oligomer. Then, the saturated alcohol formed from that step is ethoxylated. The optional step involves sulphonation of the alcohol ethoxylate formed in the preceding step. These steps will be discussed in seriatim.

Forming Alpha Olefins

Short-chain polymers of ethylene (oligomers) produced by Ziegler's ethylene chain-growth technique and recovered as linear alpha-olefins and primary alcohols in the $C_4$-$C_{20}$ range are known.

Linear alpha-olefins are produced by the cracking of normal paraffin waxes and by the oligomerization of ethylene. These are mainly precursors of plasticizer-range ($C_6$-$C_{10}$) and detergent-range ($C_{12}$ up) alcohols. Smaller quantities are used for the production of fatty amine oxides, sulfonates, thermoplastic comonomers, and synthetic lubricants.

The synthesis of alpha-olefins is based on addition of ethylene to triethylaluminum, which serves as a catalyst system wherein the ligands grow to a certain chain length by oligomerization at 80°-120° C. and 20 MPa (2900 psi) pressure. The alkyl group is then displaced by ethylene at 245°-300° C. and 0.7-2.0 MPa:

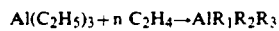

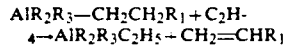

$R_1$, $R_2$ and $R_3$ are ethylene oligomers of the same or different chain lengths. Alternatively, air oxidation of these higher alkyl aluminum compounds to alkoxides followed by hydrolysis, gives straight-chain alcohols with an even number of carbon atoms:

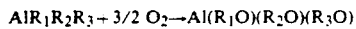

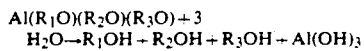

The hydration products of ethylene are ethanol and diethyl ether. The latter is produced mostly as a by-product from synthetic ethanol units.

In hyroformylation (oxo reaction) ethylene reacts with synthesis gas of a hydrogen-carbon monoxide ratio of 1:1 over a cobalt catalyst at 60°-200° C. and a pressure of 4-35 MPa (580-5075 psi) to form propionaldehyde:

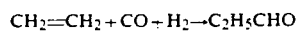

While the prior art has taught utilization of ethylene in the above processes, applicants have discovered that using propylene and/or butylene renders processes and produces products not taught here before.

ZSM-23 Catalyst

Recent developments in zeolite technology have provided a group of medium pore siliceous materials having similar pore geometry. Prominent among these intermediate pore size zeolites is ZSM-23, which may be synthesized with Bronsted acid active sites by incorporating a tetrahedrally coordinated metal, such as Al, Ga, or Fe, within the zeolitic framework. These medium pore zeolites are favored for acid catalysis. However, the advantages of ZSM-23 structures may be utilized by using highly siliceous materials or cystalline metallosilicate having one or more tetrahedral species having varying degrees of acidity. ZSM-23 crystalline structure is readily recognized by its X-ray diffraction pattern, which is described in U.S. Pat. No. 4,076,842 (Rubin, et al), incorporated by reference.

The shape-selective oligomerization/polymerization catalysts preferred for use herein include the crystalline aluminosilicate zeolites having a silica-to-alumina molar ratio of at least 12, a constraint index of about 8 to 10, and acid cracking activity (alpha value) of about 10-300. A suitable shape selective medium pore catalyst for fixed bed is a small crystal H-ZSM-23 zeolite having alpha value of about 25, with alumina binder in the form of cylindrical extrudates of about 1-5 mm. The preferred catalyst consists essentially of ZSM-23 having a crystallite size of about 0.02 to 2 microns, with framework metal synthesized as gallo-silicate, ferrosilicate, and/or aluminosilicate. These zeolites have a pore size of 4.5×5.6 Angstroms, such as to freely sorb normal hexane. In addition, the structure must provide constrained access to larger molecules.

It is generally understood that the proportion of internal acid sites relative to external acid sites increases with larger crystal size. However, the smaller crystallites, usually less than 0.1 micron, are preferred for diffusion-controlled reactions, such as oligomerization, polymerization, etc. Accordingly, it may be required to neutralize more than 15% of the total Bronsted acid sites by chemisorption of a basic deactivating agent.

The degree of steric hindrance should also be considered in the choice of the basic nitrogen compounds, especially the bulky trialkyl pyridine species having alkyl groups of 1 to 4 carbon atoms. Although the selected organonitrogen compound must be bulky enough to prevent infusion of said compound into the internal pores of the catalyst, excessive steric hindrance may prevent effective or complete interaction between the surface Bronsted acid site and the selected basic species.

Catalysts of low surface activity can be obtained by using medium pore, shape selective ZSM-23 zeolites of small crystal size that have been deactivated by one or more trialkyl pyridine compounds, such as 2,4,6-collidine(2,4,6-trimethyl pyridine, gamma-collidine). These compounds all must have a minimum cross-section diameter greater than the effective pore size of the zeolite to be treated: i.e., greater than 5 Angstroms.

When propylene or butene are oligomerized according to processes described herein, a unique mixture of liquid hydrocarbon products are formed. More particularly, this mixture of hydrocarbons may comprise at least 95% by weight of mono-olefin oligomers of the empirical formula:

$$(C_nH_{2n})_m$$

where n is 3 or 4 and m is an integer from 1 to approximately 10, the mono-olefin oligomers comprising at least 20 percent by weight of olefins having at least 12 carbon atoms, the olefins having at least 12 carbon atoms having an average of from 0.80 to 2.00 methyl side groups per carbon chain, the olefins not having any side groups other than methyl.

It will be understood that methyl side groups are methyl groups which occupy positions other than the terminal positions of the first and last (i.e., alpha and omega) carbon atoms of the longest carbon chain. This longest carbon chain is also referred to herein as the straight backbone chain of the olefin. The average number of methyl side groups for the $C_{12}$ olefins may comprise any range with the range of 0.80 to 2.00, e.g., from 0.80 to 1.90 e.g., from 0.80 to 1.80, e.g., from 0.80 to 1.70, e.g., from 0.80 to 1.60, e.g., from 0.80 to 1.50, e.g., from 0.80 to 1.40, e.g., from 0.80 to 1.30, etc.

These oligomers may be separated into fractions by conventional distillation separation. When propylene is oligomerized, olefin fractions containing the following numbers of carbon atoms can be obtained: 6, 9, 12, 15, 18 and 21. When butene is oligomerized, olefin fractions containing the following numbers of carbon atoms may be obtained: 8, 12, 16, 20, 24 and 28. It is also possible to oligomerize a mixture of propylene and butene and to obtain a mixture of oligomers having at least 6 carbon atoms.

One use for olefin oligomers described herein, particularly $C_{12}+$ fractions, is as detergent alcohols. The lower carbon number fractions, particularly $C_6-C_{12}$, make good intermediates for making plasticizer alcohols. These new olefins could possibly replace linear olefins, the current raw materials for surfactant alcohols and some plasticizer alcohols.

Page and Young (allowed application Ser. No. 105,438, filed Oct. 7, 1987) described these new olefins as multi-component mixtures of propylene oligomers having relatively few branching methyl groups on the carbon backbone. As an example of branching, the dodecene fraction prepared from propylene and HZSM-23 [ZSM23-dodecenes] typically has 1.3 methyl branches. This can be reduced to 1.0 or less by varying reaction conditions. This compares favorably with dodecenes prepared from propylene and conventional Bronsted or Lewis acids which typically have greater than 3.0 methyl branches. The projected low cost of the ZSM23-olefins, which arises from using a refinery propylene/propane stream as their starting material, makes them economically attractive. Thus, the combination of cost and structure makes ZSM23-olefins possible starting materials for biodegradable surfactant alcohols and high performance plasticizer alcohols.

Hydroformylation

Hydroformylation, a rhodium or colbalt catalyzed addition of carbon monoxide and hydrogen gas to an olefin, produces aldehydes. See J. Falbe, *New Syntheses with Carbon Monoxide*, New York (1980); E. J. Wickson, *Monohydric Alcohols*, ACS Symposium Series 159, Washington, D.C. (1981); Ford, P. C., *Catalytic Activation of Carbon Monoxide*, ACS Symposium Series 152, Washington, D.C. (1981), all references hereby incorporated by reference. However, Slaugh and Mullineaux discovered that hydroformylations using complexes of tri-n-butylphosphine and cobalt carbonyl catalyze the conversion of olefins directly to alcohols (i.e., the initially formed aldehydes concurrently hydrogenate). Also, the new alcohol function (-$CH_2OH$) bonds predominately on the carbon chain-end. See Slaugh, L., Mullineaux, R. D., *Hydroformylation Catalysts*, J. Organomet. Chem., 13, 469–477 (1968). U.S. Pat. Nos. 3,239,569; 3,239,570; 3,329,566; 3,488,158; and 3,488,157, all references hereby incorporated by reference. This permits using a variety of internal olefins as reeds, because they isomerize to a terminal position before hydroformylating. Chain-end hydroformylation maintains alcohol linearity which applicants have discovered is important for making biodegradable surfactants. In contrast, rhodium-based catalysts do not promote olefin isomerization, and hydroformylation occurs predominatly on the original double bond. See Asinger, F., Fell, B., Rupilius, W., *Hydroformylation of 1-Olefins in Tertiary Organophosphine-Colbat Hydrocarbonyl Catalyst Systems*, Chem. Process Des. Dev., 8(2), 214 (1969); Stefani, A., Consiglio, G., Botteghi, C., Pino, P., *Stereochemistry of the Hydroformylation of Olefinic Hydrocarbons with Cobalt and Rhodium Catalysts*, J. Amer. Chem. Soc., 99(4), 1058–1063 (1977). The following experiments summarize applicants' effort to prepare tridecanols by hydroformylating ZSM23-dodecenes using tributylphosphine modified cobalt-carbonyl catalyst:

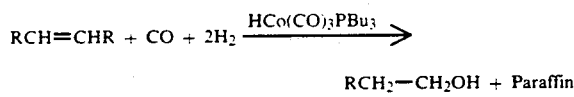

$$RCH=CHR + CO + 2H_2 \xrightarrow{HCo(CO)_3PBu_3} RCH_2-CH_2OH + \text{Paraffin}$$

EXAMPLES

The following examples throughout the remainder of this Specification illustrate embodiments of the invention without limiting it.

EXAMPLE 1

Temperature, Pressure, and Catalyst Effects on Tridecanol Yield. Using 2-level factorial designed experiments, applicants hydroformylate ZSM23-dodecenes and measure tridecanol yield while varying temperature (140° to 180° C.), pressure (200 or 1000 psig), and catalyst which is either a mixture of octacarbonyldicobalt and tri-n-butylphosphine or [Co(CO)$_3$PBu$_3$]$_2$. In the factorial design, applicants incorporate both midpoint experiments (160° C., 600 psig, using both catalysts), and subsequently, a star-point experiment (200° C., 1000 psig, using [Co(CO)$_3$PBu$_3$]$_2$ as catalyst). The ZSM23-dodecenes had 1.3 methyl branches on average, a calculated number based on analysis which showed 7% normal dodecenes, 69% monomethyldodecenes, and 24% polymethylated-dodecenes which are assumed to have 2.5 branching methyl groups. Several reaction variables are held constant including mole ratio of hydrogen gas to carbon monoxide at 2:1, dodecene to cobalt mole ratio at 80:1, and use of fresh catalyst for each batch with no recycle. FIG. 1 and Table 1 collect the tridecanol yields which vary from 24 to 70% depending on conditions. The results are 1) Increasing temperature increases yield until leveling off at 180°±/20° C.
2) Pressure between 200 and 1000 psig of the hydroformylating gas (H$_2$/CO mixture) has negligible effect on yield.
3) As a hydroformylation catalyst, the physical mixture of [Co(CO)$_4$]$_2$ and PBu$_3$ is inferior to [Co(CO)$_3$PBu$_3$]$_2$.

Increasing temperature reportedly accelerates two side reactions, olefin hydrogenation and catalyst decomposition. At 180°±/20° C., the desired alcohol producing reaction maximizes.

The relatively flat yield response to pressure changes follows the trend Slaugh and Mullineaux observed. The upper and lower faces in FIG. 1 have average yields of 49 and 47%, respectively. However, within this relatively flat yield response, changing pressure causes two small but observable trends. With [Co(CO)$_4$]$_2$ and PBu$_3$ as the catalyst precursors, yields decrease (29 to 24% and 50 to 41%) when going to higher pressure. With [Co(CO)$_3$PBu$_3$]$_2$ as catalyst precursor, yields increase (44 to 60% and 63 to 69%) when going to higher pressure. In the former, increasing pressure increases carbon monoxide concentration which presumably pushes equilibria away from [Co(CO)$_3$PBu$_3$]$_2$, the precursor which hydrogenates to active catalyst. In the latter, increasing pressure also increases hydrogen gas concentration which presumably increases hydrogenation of [Co(CO)$_3$PBu$_3$]$_2$ to active catalyst. Thus, depending upon catalyst precursor selection, changing pressure will cause small yield changes.

Compared to [Co(CO)$_3$PBu$_3$]$_2$, the mixture of (Co(CO)$_4$]$_2$ and PBu$_3$ is inferior as catalyst. The experiments on the front face of FIG. 1 used the catalyst mixture and have an average yield of 36% compared to 59% for the rear. [Co(CO)$_3$PBu$_3$]$_2$ must be synthesized. Applicants hypothesize that [Co(CO)$_3$PBu$_3$]$_2$ is an intermediate along the path to the active catalyst HCo(CO)$_3$PBu$_3$, an observable species, and [CO(CO)$_3$PBu$_3$]$_2$ forms in an equilibrium controlled reaction involving [Co(CO)$_4$]$_2$, PBu$_3$, and carbon monoxide. See, van Boven, M., Alemdarougiu, N. H., Penninger, J. M. L., *Hydroformylation with Cobalt Barbonyl and Cobalt Carbonyl-Tributylphosphine Catalysts*, Ind. Eng. Chem. Prod. Res. Develop., 14(4), 259-264 (1975); Whyman, R., *In Situ Infrared Spectral Studies on The Cobalt Carbonfl-Catalyzed Hydroformylation of Olefins*, 66, C23-C25 (1974), all references hereby incorporated by reference. Thus, the PRESENCE of carbon monoxide inhibits its formation:

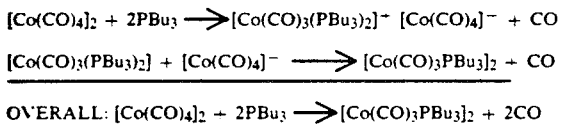

OVERALL: [Co(CO)$_4$]$_2$ + 2PBu$_3$ ⟶ [Co(CO)$_3$PBu$_3$]$_2$ + 2CO

Testing that hypothesis, applicants heat a mixture of [Co(CO)$_4$]$_2$, PBu$_3$, and ZSM23-dodecenes at 110° C. and atmospheric pressure in the absence of carbon monoxide. Applicants monitor reaction progress by infrared spectroscopy because the first-formed product, the salt (Co(CO)$_3$(PBu$_3$)$_2$]$^+$ [Co(CO)$_4$]$^-$, has two intense absorption maxima at 1997 and 1885 cm$^{-1}$, and [Co(CO)$_3$PBu$_3$]$_2$ has a single, strong absorption maxima at 1950 cm$^{-1}$. See Mirbach, M. F., Mirbach, M. J., Wegman, R. W., *Photochemical Ligand Dissociation, Electron Transfer and Metal-Metal Bond Cleavage of Phosphine-Substituted Cobalt Carbonyl Complexes*, Organometallics, 3, 900-903 (1984), hereby incorporated by reference. After one hour, the reaction solution contains only [Co(CO)$_3$PBu$_3$]$_2$.

To determine optimal tridecanol synthesis, applicants charge an autoclave with [Co(CO)$_4$]$_2$,PBu$_3$, and ZSM23-dodecenes, and heated it at 100° C. and atmospheric pressure for one hour. Then, the autoclave is pressured to 1000 psig with a hydrogen gas-carbon monoxide mixture and heated at 175°-180° C. Vacuum distillation (the usual isolation procedure) gave tridecanol in 61% yield. This compares favorably to the 41% yield obtained without pre-reaction heating (compare references 12 and 10 in Table 1), and suggests that this two-component catalyst may give yields approaching 70%, the yield achieved using [Co(CO)$_3$PBu$_3$]$_2$.

Characterization of Tridecanols. The proton-NMR derived branching index, defined as the ratio of integrals for all methyl protons to all protons expressed as a percent, indicates that these tridecanols had 1.4 branching methyl groups, nearly the same number of branching methyl groups in the ZSM23-dodecene feed. See Agrawal, K. M., Joshi, G. C., *Microcrystalline Waxes. 1. Investigations on the Structure of Waxes by Proton Nuclear Magnetic Resonance Spectrospocy*, 31, 693 (1981), hereby incorporated by reference. This implies that hydroformylation created carbon-carbon bonds on methyl groups only, because no new branches are created. Id. For method to calculate the number of branching methyl groups from the branching index. Table 2 collects physical and spectroscopic data on ZSM23-tridecanol.

Characterization of Recovered C$_{12}$'s. Not surprisingly, the cobaltcarbonylphosphine catalyst, which readily hydrogenates aldehydes to alcohols, also hydrogenates olefins to undesired paraffins. According to Slaugh and Mullineaux, paraffin formation, which typically averages 10-20%, increases with increasing reaction temperature and olefin branching. In an extreme case, hydroformylation of isobutylene gave 43% of isobutane. Applicants analyzed the recovered C$_{12}$ fraction from the 70% tridecanol yield hydroformylation (reference 11 in Table 1) looking for olefins and paraffins; this data aids in determining whether tridecanol yield can exceed 70%.

Proton NMR, $^{13}$C NMR, and bromine number determinations establish that the recovered C$_{12}$ fraction contained greater than 95% paraffin and less than 5% olefin. Two methods, infrared spectroscopy and GLPC analyses, failed. Presumably, this dilute olefin mixture of multiple isomers, each having relatively weak absorbances (C=C stretch, =C—H bending for tri-substituted olefins), kept the signal buried in the spectra's baseline. GLPC failed because of the mixture's complexity even when starting with a sub-ambient temperature program on a 50 meter capillary column.

The relatively high paraffin yield from these reactions (approx. 25%) indicates that tri-substituted double bonds, or di-substituted olefins that isomerize to tri-substituted olefins, readily hydrogenate. Assuming a methyl group is one of three substituents on these tri-substituted olefins, double bond isomerization toward the methyl carbon and addition of cobalt hydride (the active catalyst) would give an intermediate structurally similar to that formed during hydroformylation of isobutylene. Like isobutylene, the relatively high paraffin content probably results from structural features of these methyl-branched ZSM23-olefins.

Hydroformylating ZSM23-dodecene with phosphine modified cobalt carbonyl catalyst, gives tridecanol in approximately 70% yield. The balance i mostly paraffins formed by olefin hydrogenation.

Experimental

Instrumentation: Infrared spectra are recorded on a Perkin-Elmer 283 infrared spectrometer using a 3 minute scan. NMR spectra are recorded on a JEOL FX90Q using deuterochloroform as solvent and tetramethylsilane as an internal standard for proton spectra. GLPC is done on a Shimadzu GC-9A fitted with a 50 meter by 0.32 mm ID WCOT fused silica column coated with CP-SL 5CB. Flow rate is 1.8 cm/sec at 0.4 bar inlet pressure. Initial temperature is 60° C. (except for the sub-ambient runs at -15° C.) which is held for 12 min and then heated at 15° C./min until reaching 255° C. where it is maintained for 41 minutes. Injection port is maintained at 300° C. Detector is a FID.

Raw Materials: ZSM23-dodecenes are used as received. The dodecenes having 1.3 methyl branches per $C_{12}$ consisted of 85% $C_{12}$, 5% $C_{11}-$, and 10% $C_{13}+$. The 2:1 volume mixture of hydrogen gas and carbon monoxide are both CP grade. Aldrich Chemical Co. supplied tri-n-butylphosphine. It is used as received and stored under a nitrogen gas atmosphere sealed by a syringe cap. Octacarbonyldicobalt is used as received from Morton Thiokol, Alpha Products Division, and stored in a freezer at 0° F.

General Hydroformylation Procedure: A 300 mL stainless steel pressure reactor (Autoclave Engineers) is fitted with a pressure regulated hydrogen gas-carbon monoxide delivery system and vent with relief valve set at 1500 psig. Reaction temperature is monitored using a thermocouple held in a thermo-well, and maintained using a controller and an electrical heater. The reaction solution is agitated at 300 rpm with a turbine agitator. After flushing the opened autoclave with nitrogen gas, dodecene (84 g, 0.5 mole) and either catalyst A or B is charged. Catalyst A consisted of $[Co(CO)_3PBu_3]_2$ (8.63 g, 0.0125 mole) and tri-n-butylphosphine (0.6 mL, 0.51 g, 0.0025 mole). Catalyst B consisted of octacarbonyldicobalt (4.28 g, 0.0125 mole) and tri-n-butylphosphine (7.58 mL, 6.06 g, 0.03 mole). In both catalyst A and catalyst B, an excess of tributylphosphine kept the cobalt complexed with phosphine. The excesses are 0.0025 and 0.005 mole for catalyst A and B respectively. The autoclave is sealed and pressure checked with nitrogen gas while agitating. The head-space is charged to 1000 psig with hydrogen gas-carbon monoxide, and then vented to the atmosphere. This is repeated five times to exchange the head-space gases. The reactor contents are heated at the desired temperature until gas consumption ceased; the overall reaction is slighly exothermic. After cooling to room temperature, reactor contents are removed using a pipette.

Isolation of Tridecanol by Batch Distillation: Distillations are done using a glass apparatus consisting of a 2-neck, pear-shaped 100 mL flask, and a 15 cm × 150 mm insulated Vigreux column connected to a distillation head which contained a cold finger condenser and pressure equalizing stopcocks for taking fractions during vacuum distillation. Nitrogen gas is slowly bled into the distillation flask through a sub-surface glass capillary tube fitted into one of the two necks. Nitrogen gas flow is adjusted so the vacuum pump could maintain pressure at $0.5 \pm / -0.1$ mm Hg. Heat is supplied with a hot air bath constructed from a mantle-heated beaker. Prior to distillation, the crude liquid product is decanted from undissolved catalyst. Distillation of the crude liquid gave paraffins and unreacted dodecenes which are collected from 26° to 85° C. at 0.5 mm Hg. These foamed, but the Vigreux column broke the foam and prevented tridecanol from being carried into this fraction. The Vigreux column is removed after the paraffin-/olefin fraction is collected. The fraction boiling from 95° to 140° C. at 0.5 mm Hg, a water-white liquid, is collected, weighed, and labeled as tridecanol. During redistillation, a center cut is collected which boiled at 81°-83° C. at 0.15 mm (Hg).

$^1$H NMR Determination of Branching Index and Branching Methyl Groups: Applicants select the deepest valley occuring near 1.0 ppm, most frequently at 1.1 ppm, and defined methyl protons as those appearing at higher field. Branching Index (BI) is defined as the ratio of integrals for all methyl protons to all protons expressed as a percent. The total number of methyl groups in the molecule are calculated:

$$Total\ Methyl\ Groups = [BI * (n+1)]/150$$

where n = number of carbon atoms

For the tridecanols, n was taken as 13, and chain ends are defined as methyl and $CH_2OH$. Thus, the number of branching methyl groups are defined as:

$$Branching\ Methyl\ Groups = Total\ Methyl\ Groups - 1$$

Synthesis of $[Co(CO)_3PBu_3]_2$: This procedure follows that described by Manning and Forbus, but it contains more details and some minor improvements. See Manning, A. R., *Infrared Spectra of Some Derivatives of Octabarbonyldicobalt*, (A), 1135-1137 (1968); Forbus, N. P., *Kinetics and Mechanisms of Substitution Reactions of Dicolbalt Octacarbonyl*, Ph.D. Dissertation, University of Illinois, 22-32 (1980), hereby incorporated by reference. With nitrogen gas, purge a 2-neck, 500 mL round-bottom flask fitted with a reflux condenser. While sweeping the flask with nitrogen gas, charge approximately 300 mL of dry toluene. Alternately, evacuate the flask and fill with nitrogen gas. Repeat this 5 times to remove dissolved oxygen gas. Remove the octacarbonyldicobalt from the freezer and allow to warm to room temperature. Quickly weigh in the air octacarbonyldicobalt (34.2 g, 0.1 mole) and charge to the reaction flask while purging with nitrogen gas. Using a syringe, charge tri-n-butylphosphine [49.9 mL (40.4 g), 0.2 mole] into the reaction flask. Heat under reflux for 1 hour. Remove the toluene under reduced pressure, and collect the crude, deep-red $[Co(CO)_3PBu_3]_2$ by filtration; mp 60°-68° C.; mp after recrystallization from toluene 99°-102° C. (reported mp 109°-111° C.). Store in a tightly sealed gas jar shielded from light.

TABLE 1

Reaction Variable Effect on Tridecanol Yield

| Reference | Temperature (°C) | Pressure (psig) | RxTime (hr) | Catalyst | Yield (%) |
|---|---|---|---|---|---|
| 1 | 140 | 1000 | 24 | [Co(CO)4]2 + PBu3 | 24 |
| 2 | 140 | 1000 | 24 | [Co(CO)3PBu3]2 | 60 |
| 3 | 140 | 200 | 48 | [Co(CO)4]2 + PBu3 | 29 |
| 4 | 140 | 200 | 69 | [Co(CO)3PBu3]2 | 44 |
| 5 | 160 | 600 | 42 | [Co(CO)3PBu3]2 | 64a |
| 6 | 160 | 600 | 42 | [Co(CO)4]2 + PBu3 | 45 |
| 7 | 180 | 200 | 48 | [Co(CO)4]2 + PBu3 | 50 |
| 8 | 180 | 200 | 48 | [Co(CO)3PBu3]2 | 63 |
| 9 | 180 | 1000 | 24 | [Co(CO)3PBu3]2 | 69 |
| 10 | 180 | 1000 | 48 | [Co(CO)4]2 + PBu3 | 41 |
| 11 | 200 | 1000 | 48 | [Co(CO)3PBu3]2 | 70 |
| 12 | 175-180 | 1000 | 24 | [Co(CO)4]2 + PBu3 | 61b |

Notes
a-minimum yield due to handling losses during distillation
b-heated for one hour at atmospheric pressure in absence of carbon monoxide before adding $H_2$/CO

TABLE 2

Physical and Spectroscopic Characterization of ZSM23-Tridecanol (1.4 $CH_3/C_{12}$)

| | |
|---|---|
| melting range | −56 to −34° C. |
| density (25° C.) | 0.829 g/mL |
| refractive index | 1.4339 at 25° C. |
| elemental analyses (a) | Calcd for $C_{13}H_{28}O$: C. 77.93; H. 14.09; O. 7.98. Found: C. 77.63; H. 13.78 |
| boiling point | 95-140° C at 0.5 mm (Hg), center cut 81-83° C. at 0.15 mm (Hg) |
| viscosity (cSt at 40° C.) | 11.59 |
| infra-red spectrum | (neat) max. 3300 (O—H), 2900 (C—H), 1460 and 1380 (C—H bending), 1050 cm⁻¹ (C—O) |
| $^1$H NMR spectrum | (CDCl3) 3.62 (t, 1.8H, J = 5.4 Hz, $CH_2CH_2OH$), 2.0-1.1 (m, 18.8H, methylene and methine protons), 1.1-0.5 (m, 7.3 H, protons on methyl groups) |

Note
(a)-Determined by Schwarzkopf Microanalytical Laboratories, Inc. Woodside, New York

EXAMPLE 2

Improved Yield Of Tridecanol

Above, applicants made tridecanol, a valuable surfactant intermediate, in 70% yield by hydroformylating dodecene (derived from propylene and HZSM-23 catalyst). This reaction used tributyl phosphine modified cobalt carbonyl catalyst. Here applicants describe improving the tridecanol yield using phenylphosphabicyclononane modified cobalt carbonyl catalyst. Paraffin, formed by olefin hydrogenation, is the major by-product which reduces tridecanol yield. Additionally, applicants wanted to compare alcohol yields using this same catalyst and Shell Chemical olefins, NEODENE 1112 and NEODENE 1314. These olefins are feedstocks to NEODOL 25, a commerical $C_{12-15}$ detergent alcohol.

Phosphine structure significantly affects hydroformylation including alcohol yield and linearity. See U.S. Pat. No. 3,420,898; Tucci, E. R., *Hydroformylating Terminal Olefins*, Ind. Eng. Chem. Prod. Res. Dev., 9, 516-520 (1970); Pruett, R. L., Smith, J. A., *A Low-Pressure System for Producing Normal Aldehydes by Hydroformylation of Alpha-Olefins*, 34(2), 327-330 (1969), hereby incorporated by reference. Highly hindered phosphines, such as 9-phenyl-9-phosphabicyclo4.2.1-]nonane (A), 9-phenyl-9-phosphabicyclo[3.3.1]nonane (B), and 2,2,6,6-tetramethyl-1-phenylphosphorinane (C), give least paraffin and most alcohol. Applicants chose to use phenylphosphabicyclononane, a mixture of A and B. A free radical addition of a phosphine to an olefin gives phenyl-9-phosphabicyclononane and similar phosphorus compounds. See Stiles, A. R., Rust, F. F., Vaughn, W. E., *The preparation of Organo-Phosphines by the Addition of Phosphine to Unsaturated Compounds*, J. Amer. Chem. Soc., 74, 3282-3284 (1952); Rauhut, M. M., Currier, H. A., Semsel, A. M., Wystrach, V. P., *The Free Radical Addition of Phosphines to Unsaturated Compounds*, 26, 5138-5145 (1961); U.S. Pat. Nos. 3,401,204; 3,502,730, hereby incorporated by reference.

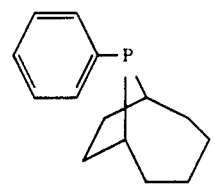

A

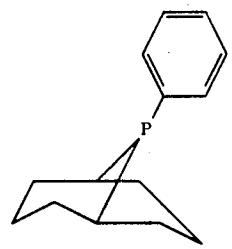

B

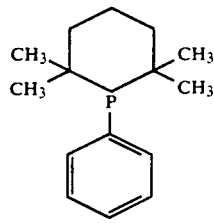

C

An improved hydroformylation of ZSM23-dodecene increased tridecanol yield from 70 to 89%. The ZSM23-dodecene came from oligomerizing propylene over HZSM-23 catalyst, and contained 1.3 branching methyl groups. The tridecanol yield equaled the yield from Shell's more linear, internal olefins (Table 3).

TABLE 3

Effect Of Phosphine Ligand And Temperature On Tridecanol Yields

| REACTION CONDITIONS | | | FEEDS: | ALCOHOL YIELDS | | |
|---|---|---|---|---|---|---|
| Temp °C. | Phosphine | P/Co ratio | | NEODOL 1112 | NEODOL 1314 | ZSM23-$C_{12}$ (1.4 $CH_3$) |
| 180 | Bu3P | 1.2/1 | | 69 | 69 | 69 |
| 180 | A + B | 1.2/1 | | 88 | 89 | 80 |
| 135/160 | A + B | 2/1 | | 85 | — | 89 |

A combination using mixture A and B as the cobalt catalyst ligand and a relatively low reaction temperature gave the improvement. A free radical addition of phenylphosphine to 1,5-cyclooctadiene gave the ligand, a mixture of A and B in a 2:1 ratio (67% overall yield).

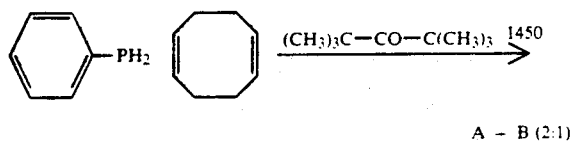

A + B (2:1)

Holding the hydroformylation reaction temperature at 135° C. for 2 hours followed by 160° C. for 48 hours gave ZSM23-tridecanol in 89% yield. The literature teaches that paraffin formation increases with increasing temperature and branching. See U.S. Pat. Nos. 3,329,566; 3,239,569; 3,239,570. Applicants observed that double bonds isomerize more rapidly than hydroformylate. Thus, applicants assume that the three competing reactions have their activation energies ranked as follows:

paraffin formation > hydroformylation > double bond isomerization

Using this assumption, applicants hypothesize that a very low initial temperature (135° C.) mainly isomerizes the double bond to a chain end. This likely distances the double bond from methyl branches. Also, a relatively low hydroformylation temperature (160° C.) reduces undesired paraffin formation. The data in Table 3 for ZSM23-dodecene supports this hypothesis. Interestingly, Shell's more linear, internal olefins, NEODENE 1112 and NEODENE 1314, gave highest alcohol yields at 180° C. and at a 1.2:1 phosphorus to cobalt ratio. For comparison, Table 3 also contains tridecanol yields using n-tributyl phosphine as the cobalt ligand. They are inferior to the improved method.

Figure 3:
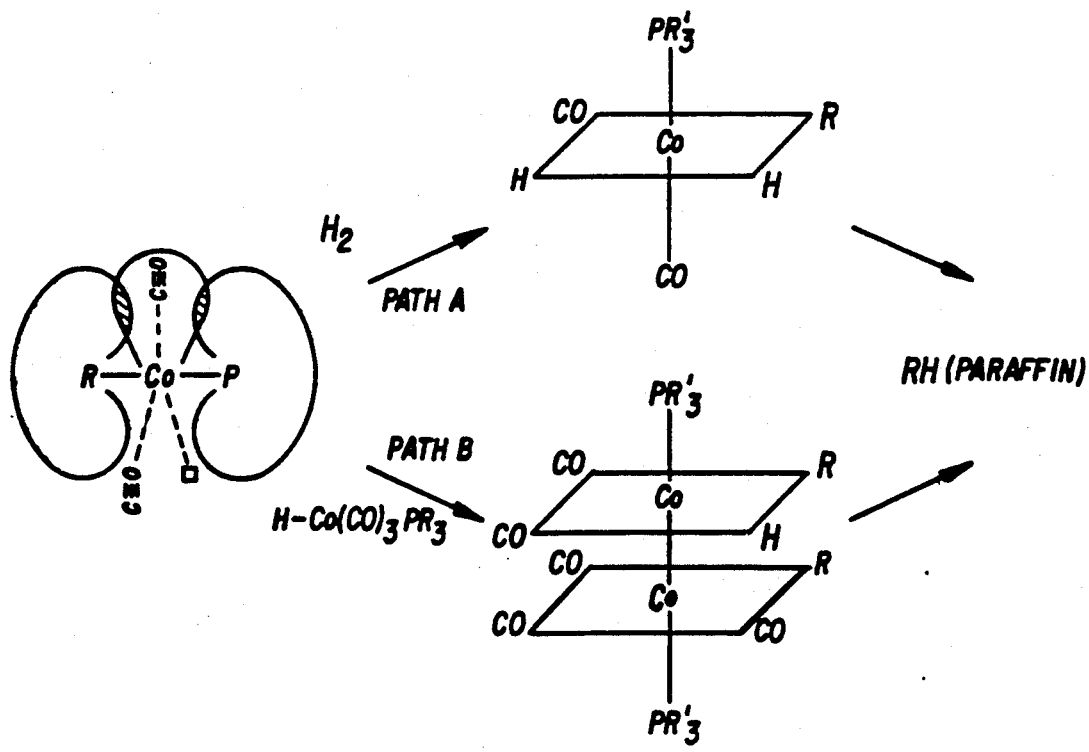
FIG. 3 depicts mechanisms for paraffin formulation.

Applicants postulate that increased steric bulk around the cobalt favors more alcohol and less paraffin. Electronic factors however, likely make a small contribution to this change. See Tolman, C. A., *Steric Effects of Phosphorus Ligands in Organometallic Chemistry and Homogeneous Catalysis*, 77(3), 313-348 (1977); Pruett, R. L., Smith, J. A., *A Low-Pressure System for Producing Normal Aldehydes by Hydroformylation of Alpha-Olefins*, 34(2), 327-330 (1969), hereby incorporated by reference. Carbon monoxide insertion can occur from a 16 electron intermediate (one vacant bonding site) while an additional CO binds to the acyl-cobalt to maintain 16 valence electrons. Forming the acyl-cobalt relieves steric strain in the 16 electron intermediate by separating the phosphine ligand and olefin moiety (FIG. 2). According to the literature, hydrogenation occurs by either adding hydrogen gas and forming a dihydrido intermediate (path a, FIG. 3) or inserting the cobalt into another cobalt hydride (path b, FIG. 3). The latter path gives a bimetallic cobalt complex. In either path, a congested 18-electron intermediate precedes paraffin formation. This increases hydrogenation activation energy relative to carbonylation, and it results in less paraffin and more alcohol.

Hydroformylation of ZSM23-dodecene gave tridecanol in 89% yield. Using 9-phenyl-9-phosphabicyclononane as the cobalt catalyst ligand and relatively low reaction temperatures increased the alcohol yield by reducing paraffin formation.

Hydroformylation Procedure

The general procedure is described in Example 1. Table 3 contains reaction conditions and reactant and catalyst ratios.

Preparation of 9-Phenyl-9-Phosphabicyclononane

This procedure is a modification of Mason and Van Winkle's. See U.S. Pat. No. 3,400,163. All glassware is dried at 120° C. and assembled hot under a purge of argon. A 250 mL, 3-neck flask is fitted with magnetic spin bar, thermometer, reflux condenser, a rubber syringe septum, argon inlet, and flowmeter. The reactor system is purged overnight with argon flowing at 3 mL/min., and then charged with redistilled 1,5-cyclooctadiene [43.3 g (49.1 mL), 0.4 mole, density=0.882 g/mL, from Aldrich Chemical Co.] and phenylphosphine [44.0 g (44.0 mL), 0.4 mole, density=1.00 g/mL, from Strem Chemicals] while under a stream of argon. The reaction solution is heated to 135° C. Di-t-butylperoxide [1.46 g (1.8 mL), 0.01 mole, density=0.796 g/mL, from Aldrich Chemical] is mixed with 5 mL of undecane and added with a syringe pump over 1 hour while maintaining the temperature of the exothermic reaction at 135°-145° C. A second portion of di-t-butylperoxide (1.8 mL in 5 mL of undecane) is added rapidly, and the temperature is increased to 150° C. and held for an additional hour. Periodic aliquots, taken with a syringe through the septa, are examined by infrared spectroscopy, and the disappearance of the olefin band at 1645 $cm^{-1}$ and the P-H band at 2300 $cm^{-1}$ is monitored. After two hours total reaction time, both of these bands had disappeared. The reaction mixture is distilled through a 6-inch Vigreux column and a mixture, 58.3 g (67%) of 9-phenyl-9-phosphabicyclo[4.2.1]nonane and 9-phenyl-9-phosphabicyclo[3.3.1-]nonane, is collected [b.p. 123-125·at 0.1 mmHg], and stored in a refrigerated and septum-sealed flask under a nitrogen gas atmosphere. Reported b.p.: 134°-135° C. at 0.3 mm (Hg). Gas chromatography shows the mixture is 67% 9-phenyl-9-phosphabicyclo[4.2.1]nonane (the earlier eluting isomer) and 33% 9-pheny-9-phosphabicyclo[3.3.1]nonane.

EXAMPLE 3

Esters Made From Tridecanol

Applicants synthesized bis-tridecanol esters of adipic and phthalic acid for use as plasticizes and synthetic lubricants. Applicants used two tridecanols, one with relatively low and one with a relatively high degree of methyl branching. The more linear tridecanol came from the hydroformylation of dodecene which originated from propylene using HZSM-23 discussed above. This alcohol contained 1.4 branching methyl groups. Isotridecanol came from Exxon Chemical and contained 3-4 branching methyl groups. The phthalate and adipate made from isotridecanol are Mobil lubricants.

TABLE 4

Synthetic Lubricants:
Comparison of Tridecyl Phthalates and Adipates

|  | Diisotridecyl-phthalate[a] | Ditridecyl-phthalate[b] | Diisotridecyl-adipate[a] | Ditridecyl-adipate[b] |
|---|---|---|---|---|
| cSt 40° C. | 83 | 43.5 | 26.9 | 21.2 |
| cSt 100° C. | 8.2 | 6.1 | 5.3 | 4.8 |
| Pour Point | <37 C. | −54 C. | −65 C. | −37 C. |

[a] made from isotridecanol containing 3-4 branching methyl groups
[b] made from tridecanol containing 1.4 branching methyl groups A 500 mL, 3-neck round bottom flask is equipped with a magnetic stirrer, Dean-Stark water trap, and reflux condenser with a drying tube containing magnesium sulfate. The flask is charged with toluene (250 mL), phthalic anhydride (22.2 g, 0.15 mole), tridecanol (60.11 g, 0.3 mole, containing 1.4 branching methyl groups), and p-toluene sulfonic acid (0.1 g). The reaction is heated under reflux for 20 hours. Three milliliters of water is collected. Removing the solvent under a reduced pressure gave 78.2 g (95%) of ditridecylphthalate, a yellow liquid whose viscosity at 40° C. is 43.5 centistokes.

In comparison, isotridecyl alcohol, which contains 3-4 branching methyl groups, and phthalic anhydride give a product whose viscosity at 40° C. is 83 centistokes. These data show that the more linear alcohol gives a product with improved low temperature properties. Also, one skilled in the art recognizes that more linear alcohols decrease the volatility of esters such as this phthalate. These properties are useful for plasticizing PVC and other plastics. Ditridecylphthalate is also useful as a high temperature lubricant, and finds application in jet engines among other places.

A 250 mL, 3-neck round bottom flask is equipped with a magnetic spin bar, thermometer, rubber septum, nitrogen gas injector, and reflux condenser with exit port. Tridecanol (60.11 g, 0.3 mole, containing 1.4 branching methyl groups) is charged into the flask, and adipoyl chloride (27.45 g, 0.15 mole, purchased from Aldrich Chemical) is added portionwise from a syringe. A slow, continuous nitrogen gas purge swept hydrogen chloride which began to evolve after adding about half the adipoyl chloride. The reaction exothermed to 67° C. After completing the adipoyl chloride addition, the reaction mixture is maintained at 150° C. for 14 hours. The yield is 73.3 g (96%) of a brown liquid. Viscosity at 40° and 100° C. is 21.2 and 4.8 centistokes, respectively (viscosity index=159).

In comparison, isotridecyl alcohol, which contains 3-4 branching methyl groups, and adipoyl chloride gave a product whose viscosity at 40° and 100° C. is 26.9 and 5.3 centistokes, respectively (viscosity index=134). Those skilled in the art generally prefer lubricants with a higher viscosity index.

Table 4 compares the viscometric and pour point data of the four esters. The more linear tridecyl esters are markedly less viscous at 40° C. This demonstrates their excellent low temperature properties, and makes them useful, for example, in maintaining PVC flexibility at ambient and subambient temperatures. The highly branches esters, however, have lower pour points which makes them useful lubricants for engines subjected to very cold temperatures. Ester linearity improves the Viscosity Index (VI), especially of the adipates where VI's of the branched and linear esters are 134 and 159 respectively. Ester linearity also decreases ester volatility and extraction by detergents, two important properties for some plasticizers.

EXAMPLE 4

Preparation of Tridecanol Ethoxylates As Nonionic Surfactants

Here applicants describe making tridecanol-ethoxylates containing about 8-9 moles of ethylene oxide per alcohol, a level frequently used for nonionic surfactants. Tridecanol-ethoxylates and other alcohol-ethoxylates are large volume chemicals used in the growing, surfactant market.

In the presence of potassium alcoholate as catalyst, alcohols and ethylene oxide react exothermically to form alcohol-ethoxylates (equation). Although their ethylene oxide content typically reflects the original feed ratio, these ethoxylates have a molecular weight distribution. In reactions using catalytic amounts of potassium alcoholate, the relative acidities of the starting alcohol and the alcohol-ethoxylate control the distribution's width. Compared to phenols, aliphatic ethoxylates have broader distributions because the ethoxylates are more acidic than the alcohols themselves. In other words, an ethoxylating chain prefers either to grow or deprotonate another alcohol-ethoxylate rather than deprotonate a starting alcohol. This generates a mixture containing long to short-chained ethoxylates.

For alcohol-ethoxylates, hydroxyl number gives number-average molecular weight. Chromatographic methods give both weight- and number-average molecular weights. The chromatographic methods include TLC of dinitrobenzoate esters, GLPC of acetate and silyl esters, and phenylcarbamate esters. See Gildenberg, L., Trowbridge, J. R., *Gas-Liquid Chromatographic Separation of Ethylene Oxide Adducts of Fatty Alcohols Via Their Acetate Esters*, J. Amer. Oil Chem. Soc., 42, 69-71 (1965); Tornquist, J., *Separation by Gas Chromatography of Alcohol-Ethylene Oxide Adducts*, Acta Chem. Scandinavica, 20, 572-573 (1966); Allen, M. C., Lunder, D. E., *Ethylene Oxide Oligomer Distribution in Nonionic Surfactans via High Performance Liquid Chromatography*, J. Amer. Oil Chem. Soc., 58(10), 950-957 (1981), hereby incorporated by reference. The following describes preparation of tridecanol-ethoxylates and their analyses by hydroxyl number and GLPC of their acetate esters.

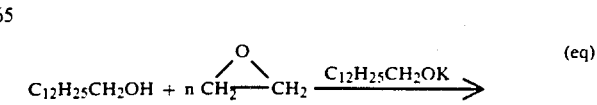

-continued $$C_{12}H_{25}CH_2(OCH_2CH_2)_nOH$$

Alcohol-Ethoxylate Syntheses. Table 5 summarizes synthesis data on four tridecanol-ethoxylates and one mixed alcohol-ethoxylate. The tridecanols themselves had varying degrees of branching methyl groups which affect biodegradation, an important consideration for many surfactant uses. Applicants prepare and ethoxylate tridecanols containing an average of about 1 to 2.5 branching methyl groups in Example 1. Two model compounds bracketed the methyl branching of applicants' tridecanols. 1-Tridecanol is perfectly linear, and tridecyl alcohol (EXXAL 13) from Exxon Chemical has 3–4 branching methyl groups. Applicants also ethoxylate NEODOL 25 (a mixture of $C_{12-15}$ alcohols having 1.1 methyl branches). Applicants compare the product with NEODOL 25-9, one of Shell Chemical's commercially available alcohol-ethoxylates containing nine moles of ethylene oxide. The comparison tests ability both to make and analyze alcohol-ethoxylates.

TABLE 5

| ALCOHOL | REFERENCE | RxPRESS psig | RxTEMP deg C. | EO Add TIME, hrs | YIELD | % PEG |
|---|---|---|---|---|---|---|
| NEODOL 25 | 1 | 75–90 | 135–140 | 4.5 | 89 (a) | 6 (a) |
| | 2 | 75 | 135–140 | 6. | 93 (b) | 3 (b) |
| EXXAL 13 | 3 | 85–110 | 135–165 | 3.5 | 95 (a) | 10 (a) |
| TRIDECANOL (1.4) | 4 | 85–110 | 135–150 | 4.25 | 95 (a) | 7 (a) |
| | 5 | 75 | 135–140 | 6. | 95 (b) | 7 (b) |
| TRIDECANOL (2.4) | 6 | 95–110 | 135–150 | 3.75 | 99 (a) | 11 (a) |
| TRIDECANOL-1 | 7 | 70–95 | 137–141 | 16. | 74 (a) | 5 (a) |
| | 8 | 75 | 135–140 | 6. | 95 (b) | 4 (b) |

Notes
(a)-Potassium hydroxide used as catalyst precursor
(b)-Potassium t-butoxide used as catalyst precursor Potassium tridecanolate in tridecanol, generated by adding potassium hydroxide and removing the water formed, oligomerized ethylene oxide. The ethylene oxide slowly added as liquid while maintaining the pressure below 100 psig and the temperature between 135°–145° C. In three cases, applicants observe a delayed exotherm after adding all the ethylene oxide. In those instances, the temperature and pressure increased to 150°–165° C. and 110 psig respectively. Operating below 90 psig (usually at 75 psig) reduced the large exotherm. Presumably, the reaction proceeded more slowly and the heat released over longer time. Isolated yields are excellent, 89–99%, excepting the ethoxylate of tridecanol-1 (74%). Here, applicants presume that ethylene oxide escapes through a leak because resynthesis gave the ethoxylate in 95%.

An extractive procedure shows that the five laboratory-prepared alcohol ethoxylates contained 5–11 wt % polyethylene glycol (PEG). In comparison, NEODOL 25-9, a typical commerical alcohol-ethoxylate, contained only 0.3 wt % PEG. Initially, applicants suspect that residual potassium hydroxide, left by an incomplete reaction of potassium hydroxide and alcohol, oligomerizes ethylene oxide making PEG. Repeating three syntheses using potassium t-butoxide, a more alcohol-soluble potassium source, reduces the average PEG content to 5% (3 trials). Although a reduction, applicants still had to find the hydroxide source which generated PEG. Water analysis shows 3700 ppm water in the tridecanol and 3855 ppm water in NEODOL 25. Assuming 600 average molecular weight for PEG, these water levels would theoretically generate 4.1 and 4.3 wt % PEG, respectively. These are close to the experimentally observed 4 and 3 wt %. Thus, to minimize PEG content in alcohol-ethoxylates, applicants believe the alcohol must be dry.

Figure 4A:
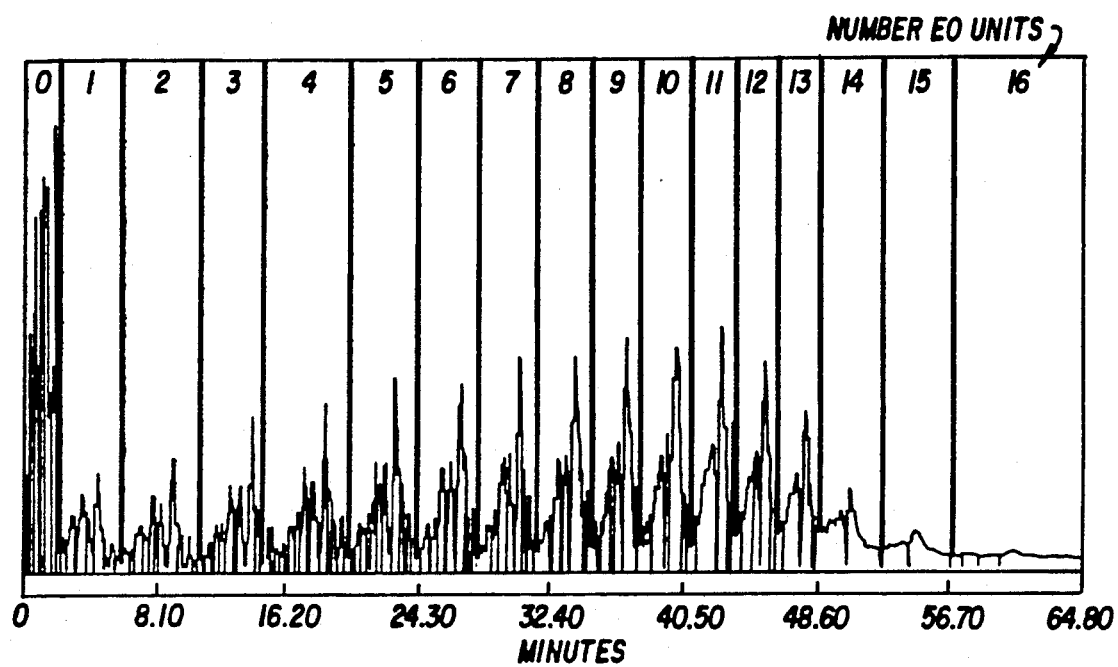
FIGS. 4A and 4B depict GLPC's of two alcohol-ethoxylates as their acetate esters.
Figure 4B:
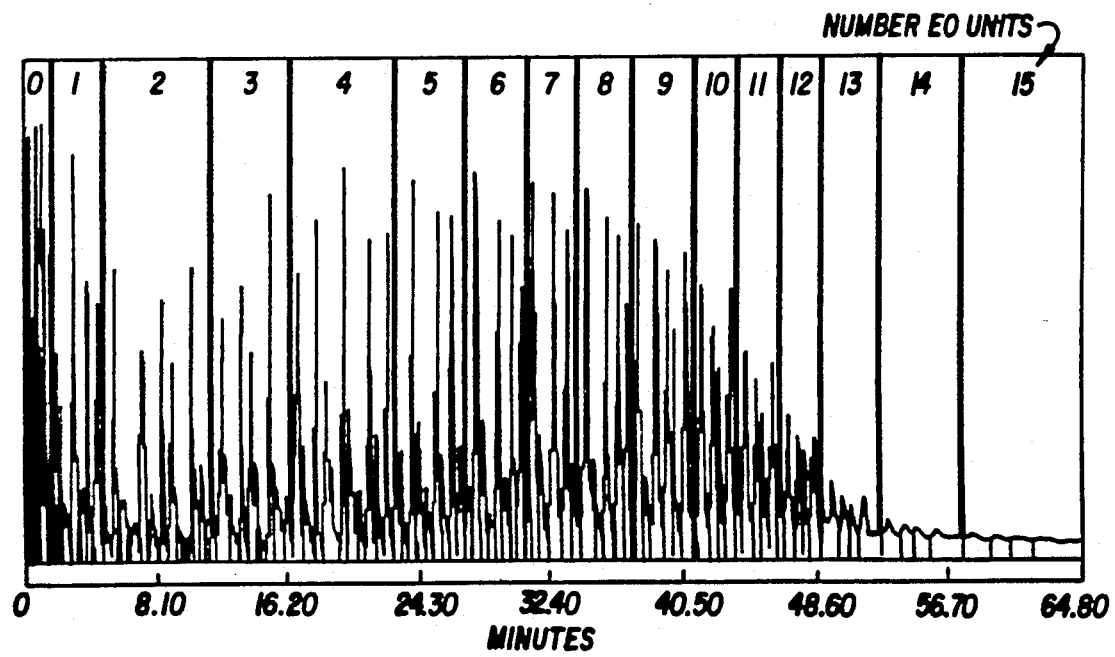

Analyses of Alcohol-Ethoxylates. Modifying Gildenberg and Trowbridge's procedure gave an improved GLPC method for determining ethylene oxide distributions on alcohol-ethoxylates. Id. The ethoxylates, as their acetate esters, separate by number of ethylene oxide units (rather than by alcohol isomers). The method uses a relatively short (10.5 meter) fused silica capillary column which is temperature programmed and then held at 330° C. for 2.5 hours. This method routinely detected individual alcohols containing 19 ethylene oxide units (Gildenberg and Trowbridge routinely detected alcohols with 12 or fewer ethylene oxide units). Ethoxylates containing more than 19 ethylene oxide units eluted during the hold time. The instrument detected them as an undifferentiated signal above base line. Although the method's upper limit remains unknown, applicants analyze alcohol-ethoxylates containing, on average, 8-9 ethylene oxide units. FIG. 4 shows GLPC's of two representative ethoxylates.

Using this GLPC method and a standard hydroxyl number determination, applicants analyze laboratory- and commercially-prepared NEODOL 25-3 and NEODOL 25-9. NEODOL 25-3 contains three moles of ethylene oxide. Table 6 contains these analyses and typical values from a Shell Chemical Company product bulletin (Table 6). Applicants believe their typical analyses uses, besides hydroxyl number, McClure's HPLC method. The number-average molecular weights (Table 6) determined by both methods differed by 2-22%. Also, samples of NEODOL 25-3 and NEODOL 25-9 have lower molecular weights and ethylene oxide content than typical values (Table 6). This likely reflects batch-to-batch variations which the NEODOL 25-9 sales specification reflects: 8.4 to 10.2 ethylene oxide units. Table 6 also shows that our laboratory-prepared NEODOL 25-9 lies between purchased and typical NEODOL 25-9 samples. This demonstrates applicants can synthesize commerical-like ethoxylates. Next, applicants apply these methods to tridecanol-ethoxylates.

TABLE 6

| | Analysis Of NEODOL-Ethoxylates | | | | |
|---|---|---|---|---|---|
| | NEODOL 25-3 | | NEODOL 25-9 | | |
| | SHELL typical | MOBIL ANAL | SHELL typical | MOBIL ANAL | MOBIL PREP |
| Mw/Mn (a) | 376/329 | 339/286 | 665/577 | 561/457 | 575/478 |
| Moles EO (b) | 2.9 | 1.9 | 8.5 | 5.8 | 6.3 |
| Hydroxyl No. | 167.0 | 180.7 | 92.0 | 97.2 | 91.5 |

TABLE 6-continued

| Analysis Of NEODOL-Ethoxylates | | | | |
|---|---|---|---|---|
| NEODOL 25-3 | | NEODOL 25-9 | | |
| SHELL typical | MOBIL ANAL | SHELL typical | MOBIL ANAL | MOBIL PREP |
| Mn (c) 336 | 310 | 610 | 577 | 613 |
| Moles EO (d) 3.0 | 2.4 | 9.2 | 8.5 | 9.3 |

Notes
(a) Determined Mw and Mn by chromatography using 203 as NEODOL 25 mol wt
(b) Calculated moles of EO from chromatographically determined Mn. Moles EO = (Mn-203)/44
(c) Calculated Mn from hydroxyl number. Mn = 56100/OH#
(d) Calculated moles of EO from Mn determined by Hydroxyl Number. Moles EO = (Mn-203)/44

Like the NEODOL-ethoxylates, the tridecanol-ethoxylates gave different molecular weights depending on the method used (Table 7). The ethoxylates of 1-tridecanol and EXXAL 13 show 12-15% differences between the GLPC and hydroxyl number methods. Both 1.4- and 2.4-methyl branched tridecanol-ethoxylates have 37-39% method-dependent differences. The reason for these latter, relatively large, differences remains unknown. Applicants believe the molecular weights determined by chromatography (in both Tables 6 and 7) are low, but applicants favor this method. It gives results which, after a correction, more consistently agree with the stoichiometry and isolated yields. However, only further analytical work will reconcile these differences.

TABLE 7

| Analyses of Tridecanol-Ethoxylates | | | | |
|---|---|---|---|---|
| STARTING ALCOHOL | C130H-1 | (1.4 CH3)C130H(a) | (2.4 CH3)C130H(a) | EXXAL 13(b) |
| ETHOXYLATE: | | | | |
| Mw/Mn(c) | 636/520 | 583/469 | 612/496 | 591/495 |
| Moles EO(d) | 7.3 | 6.0 | 6.7 | 6.6 |
| Hydroxyl No. | 120.4 | 73.4 | 70.7 | 96.5 |
| Mn(e) | 466 | 764 | 793 | 581 |
| Moles EO(f) | 6.0 | 12.8 | 13.4 | 8.6 |

Notes
(a)Used 202 as average mol wt
(b)Used 200 as average mol wt
(c)Determined Mw and Mn by chromatography
(d)Calculated moles of EO from chromatographically determined Mn. Moles EO = (Mn-alcohol MW)/44
(e)Calculated Mn from Hydroxyl Number. Mn = 56100/OH#
(f)Calculated moles of EO from Mn determined by Hydroxyl Number. Moles EO = (Mn-alcohol MW)/44.

Tridecanols, prepared from ZSM23-oligomerized propylene, exothermically react with ethylene oxide forming tridecanol-ethoxylates. Other tridecanols, both more and less methyl-branched than the ZSM23-tridecanols, also readily ethoxylate. A GLPC method, which gives molecular weight, and ethylene oxide content of these alcohol-ethoxylates, show them comparable to a commercial standard.

Raw Materials. The synthesis of tridecanol from ZSM23-dodecene is described previously in Example 1. 1-Tridecanol is purchased from Aldrich Chemical. EXXAL 13 is obtained from Exxon Chemical Co. NEODOL 25, NEODOL 25-3, and NEODOL 25-9 are obtained from Shell Chemical Co. Ethylene oxide is purchased from Matheson Gas Products. All raw materials are used as received.

Procedure for Ethoxylating Tridecanols. This procedure follows those by Satkowski and Hsu, and a Shell Chemical Company Bulletin, see Ind. Eng. Chem.; Satkowski, W. B., Hsu, C. G., "Polyoxyethylation of Alcohol", 1957, 49, 1975, and describes synthesizing a tridecanol-ethoxylate containing nine ethylene oxide residues. A 500 mL autoclave is charged with tridecanol [50 g (approximately 60 mL), 0.25 mole] and potassium hydroxide (0.15 g, 0.00268 mole), and heated at 135° C. under vacuum (15 mm Hg or lower) for one hour. This removes water. Nitrogen gas is added until the vessel's pressure is 45 psig. Liquid ethylene oxide [99 g (113 mL), 2.25 mole] is fed on pressure demand from a calibrated, nitrogen gas blanketed Jurgenson gauge which is fitted with a check valve. Ethylene oxide flowed once the reactor's pressure dropped below the pressure of the nitrogen gas blanket. Temperature is maintained at 135°-150° C. (exothermic), and pressure kept at less than 100 psig, typically 75 psig. After all the ethylene oxide is added and the pressure approached a steady value, typically 50 psig, the cooled (<60° C.) product is transferred to a nitrogen gas filled bottle that contained sufficient glacial acetic acid (0.161 g, 0.00268 mole) to exactly neutralize the potassium alkoxide catalyst. The product is not purified further, but taken as 100% active material. The product volume (approximately 150 mL) is less than the sum of the reactants because its specific gravity increased to approximately 0.98 g/mL.

Acetylation of Alcohol-Ethoxylates. Applicants followed McClure's procedure which is summarized here. McClure, J. D., Determination of Ethylene Oxide Oligomer Distributions in Alcohol Ethoxylates by HPLC Using a Rotating Disc-Flame Ionization Detector. Presented at the AOCS Meeting, New Orleans, May 1981. Also, Shell Chemical Co. Technical Bulletin SC:580.82. The above-references are hereby incorporated by reference. An acetylation reagent is prepared by slowly adding acetic anhydride (120 mL) with stirring to a solution of p-toluene sulfonic acid monohydrate (14.4 g) and ethyl acetate (360 mL). This reagent is stored in a tightly sealed bottle shielded from light. A 100 mL flask, equipped with a magnetic spin bar and drying tube, is purged with nitrogen gas. Four grams of alcohol-ethoxylate is dissolved in 4 mL of toluene and transferred to the flask along with 12 mL of acetylation reagent. This solution is heated at 50° C. for 30 minutes, transferred to a separatory funnel along with 40 mL of toluene, and washed three times: 100 mL of 30 wt % brine; 100 mL of bicarbonate-brine (50 g sodium bicarbonate, 250 g sodium chloride, 1750 g water); 100 mL of 30 wt % brine. The toluene solution is dried (magnesium sulfate), filtered, and evaporated under reduced pressure giving acetylated alcohol-ethoxylate, a viscous liquid.

GLPC Analysis of Acetylated Alcohol-Ethoxylates. GLPC of acetylated alcohol-ethoxylates is done on a Shimadzu GC-9A fitted with a 10.5 meter micro-capillary fused-silica column coated with OV-11. Helium is the carrier gas flowing at 365 cc/min through a 10:1 pre-column splitter. Flow through the column is not measured. Initial temperature is 150° C. which is held for 3 min and then heated at 4° C./min until reaching 330° C. where it is maintained for 152 minutes. Injection port is maintained at 300° C., and detector is a FID. Integrations are done using a Hewlett Packard Laboratory Data System 3357. The undifferentiated signal above base line, which eluted after the ethoxylate containing 18 or 19 ethylene oxide units, is assigned 1000 MW. It is treated as a single peak for calculations. The response factor is taken as unity for all peaks. $M_w$'s are calculated by summing the products of molecular weight and weight fractions for each peak ($M_w$ of the peak multiplied by its weight percent). $M_n$'s are calculated by summing the products of the mole fraction and the molecular weight for each peak.

Determination of PEG in Ethoxylates. Applicants followed a Shell Chemical Company procedure which is summarized here. Ethyl acetate (50 mL), brine (50 mL containing 0.29 g sodium chloride/mL), and alcohol-ethoxylate (10 grams weighed to nearest 0.01 g) is transferred to a 250 mL separatory funnel which is stoppered, shaken for 2 min and allowed to stand for 15 minutes. All subsequent extractions followed this shake/stand procedure. The lower brine phase is transferred to a second separatory funnel. The ethyl acetate solution is extracted a second time with 50 mL of brine. The combined brine extracts are back-extracted twice with 50 mL portions of chloroform, and the chloroform layers (bottom) are filtered through a plug of cotton, are dried over anhydrous magnesium sulfate, and are evaporated to dryness in a tared (to nearest milligram) 150 mL flask. Acetone (10 mL) is added to check for the presence of sodium chloride seen as suspended crystals. If present, they are removed by filtration. The acetone is evaporated from a tared flask. The residue is dried in a vacuum oven at 50° C. and 200-300 mm Hg for one hour. After cooling to room temperature in a desiccator, the final weight of recovered PEG is taken by difference from the tared flask. The percent PEG is calculated by dividing the weight of recovered PEG by 10 (weight of original sample) and multiplying by 100.

Hydroxyl Number Determination. The pyridine-acetic anhydride ASTM procedure is used except the acetylation time is increased from 30 to 60 minutes.

EXAMPLE 5

Comparison of Tridecanol Ethoxylate To Commercial Standards In Household And Industrial Laundry Detergents Synthesizing tridecanol-ethoxylates from dodecenes prepared from propylene using HZSM-23 catalyst are described in Examples 1-3. These are tested as surfactants in two laundry detergents.

Detergency evaluations have evolved into systematic and miniaturized procedures. See Kissa, E., *Detergency Evaluation*, Detergency Theory and Technology, Marcel Dekker, Chapter 1, New York (1987), hereby incorporated by reference. Initial tests no longer require actual wash loads (although final evaluations still do). Test fabrics with uniformly applied artificial soils are commercially available. A Terg-O-Tometer, for example, washes small swatches while controlling temperature and agitation speed. This requires only one liter of test solution. Reflectance readings, taken before and after washing, measure percent soil removal. Applicants evaluate tridecanol-9 mole-ethoxylate, as a surfactant in a phosphate built industrial detergent and in a non-built household detergent. Commercial standards, $C_{12-15}$-alcohol-9 mole-ethoxylate and dodecylbenzenesulfonic acid sodium salt, serve as comparisons.

Detergent Type and Composition. The industry classifies laundry detergents according to end-use market (industrial or household), physical form (liquid or powder), and builder (built or non-built). Builders are further classified as either phosphate or non-phosphate containing. From this array, applicants select two for making surfactant comparisons, an industrial liquid built with phosphates and an unbuilt household liquid. The convenience of liquid detergents (dispensing and mixing ease, and opportunity to apply detergent concentrate to spots before washing) is contributing to their rapid growth. This influences selecting two liquids. Manufacturers prefer phosphate builders, but where laws limit or ban their use, alternatives are used (usually at a performance penalty). This experiment uses a phosphate built industrial detergent to maximize soil removal, and a non-built household detergent to maximize surfactant differences.

Applicants blend three unbuilt household detergents differing only in the surfactant. Either Mobil's tridecanol-9 mole-ethoxylate, Shell's $C_{12-15}$-alcohol-9 mole-ethoxylate, or Vista's dodecylbenzenesulfonic acid sodium salt are used. All contain triethanolamine to make the wash liquor basic. This type formulation magnifies surfactant differences because it lacks a builder to extend the surfactant and soften hard water.

In contrast, the three industrial detergents contained a high performance builder package, and dodecylbenzenesulfonic acid sodium salt. Two of the three also contain an AE, either tridecanol-9-mole-ethoxylate or $C_{12-15}$-alcohol-9 mole-ethoxylate. Many commercial detergents use combinations of LABS and AE's to balance performance and cost. LABS remove particulates well and lower overall surfactant cost while AE's effectively remove oily soils. The surfactant concentrations in all three are equal (i.e., the detergent without AE had more LABS) excepting the detergent using Mobil's AE. Its concentration is not increased to offset a contaminant, 7 wt % polyethylene glycol. The builder in all three detergents contained tetrapotassium pyrophosphate, sodium metasilicate, potassium hydroxide, and carboxymethylcellulose.

Raw Materials. Mobil's tridecanol-9 mole-ethoxylate is prepared from tridecanol having 1.4 branching methyl groups; it contains 7 wt % PEG. Shell Chemical supplied a sample of their $C_{12-15}$-alcohol-9 mole-ethoxylate as NEODOL 25-9. Vista Chemical supplied a 50 wt % sample of their dodecylbenzenesulfonic acid sodium salt as C-550. Hercules supplies carboxymethylcellulose as CMC 7LT. PQ supplies sodium metasilicate pentahydrate as Metso granular.

Testing Methods. This study uses two artificial soils on three test fabrics. Carbon black in an oil matrix simulates particulate soil, and sebum/dust simulates oily soil. Test Fabrics Inc. (Middlesex, N.J.) prints these soils on 100% cotton, 65/35 polyester/cotton with permanent press finish, and 100% polyester fabrics.

U.S. Testing Company did the fabric washing and drying under carefully controlled conditions. A Terg- O-Tometer washes using a 15 minute wash time. Conditions are 100 rpm agitation speed, 130° F. for the industrial detergents and 100° F. for the household detergents. They made wash and rinse water to 150 ppm hardness (U.S. national average), and washes six 3×4 inch test swatches per liter of solution. They rinse each load twice for five minutes. After washing and rinsing, the swatches are dried in an electric dryer, and ironed with a warm iron to remove wrinkles. All samples are run in triplicate.

White light reflectance, taken before and after washing, measures soil removal. A green filter cut out the effect of artificial brighteners. They measure soil redoposition by taking reflectance readings of fabric margins (areas not printed with soil) before and after washing. Radio tracer methods provide a superior alternative to the reflectance technique for measuring TOTAL soil removal. See Shebs, W. T., *Radioisotope Techniques in Detergency*, Chapter 3, Marcel Dekker, New York (1987). However, the reflectance technique more closely measures soil removal from the fabric surface, what the consumer sees.

Soil Removal and Redeposition. Tables 8 and 9 and FIGS. 5 and 6 summarize soil removal data. The industrial detergents clearly out-performed their household counterparts which shows the benefits of builder, surfactant combinations, and higher wash temperature. For sebum removal, the AE's are superior to LABS. For particulate removal, AE/LABS combination show a synergy and out-performed LABS itself in the industrial formulation. However, as unassisted individual surfactants (household detergents), LABS removes more particulates. These results experimentally confirm what the market place has been saying, namely, AE's are excellent surfactants especially for removing sebaceous soil. Matson, T. P., *Monohydric Alcohols*, Wickson, E. J. Ed., ACS Symposium Series 159, American Chemical Society, Washington, D.C., 101-112 (1981), hereby incorporated by reference.

TABLE 8

Percent Soil Removal Phosphorous Built Industrial Liquid Laundry Detergent

| SOIL AND FABRIC | SURFACTANTS | | |
|---|---|---|---|
| | Mobil AE + Vista LABS | Shell AE + Vista LABS | Vista LABS |
| Carbon Black/Oil | | | |
| Cotton | 51 | 58 | 52 |
| Polyester/Cotton | 43 | 49 | 34 |
| Polyester | 48 | 50 | 29 |
| Sebum/Dust | | | |
| Cotton | 64 | 67 | 60 |
| Polyester/Cotton | 85 | 89 | 82 |
| Polyester | 57 | 57 | 39 |

TABLE 9

Percent Soil Removal Unbilt Household Liquid Laundry Detergent

| SOIL AND FABRIC | SURFACTANTS | | |
|---|---|---|---|
| | Mobil AE | Shell AE | Vista LABS |
| Carbon Black/Oil | | | |
| Cotton | 23 | 24 | 36 |
| Polyester/Cotton | 24 | 25 | 31 |
| Polyester | 22 | 21 | 40 |
| Sebum/Dust | | | |
| Cotton | 48 | 58 | 36 |
| Polyester/Cotton | 62 | 65 | 45 |
| Polyester | 29 | 29 | 19 |

Comparing Shell Chemical's $C_{12-15}$-alcohol-9 mole-ethoxylate and Mobil's ZSM23-tridecanol-ethoxylate, the two surfactants are very comparable in the two laundry detergents tested. Closer examination shows that the Shell AE removed 4-7% more soil in 4 of the 12 tests. Differences greater than 3% are statistically significant. However, if concentrations are taken into account (i.e., the soil removed with the Mobil AE are increased 7%), then the Mobil AE performed equally to the Shell AE, an industry standard.

Tables 10 and 11 collect redeposition indexes (or white retention values) for the industrial and household detergents, respectively. These indexes quantitate soil removed from soiled fabric and redeposited on unsoiled fabric. A ratio of reflectances taken before and after washing unsoiled cloth gives the redeposition index. Higher values mean better performance, and readings of 98-100 are good. Values of 94-95 (or lower) show noticeable redeposition. All test specimens gave redeposition indexed of 96 or higher expect one, the Shell AE. It had a redeposition index of 95 in the industrial detergent cleansing sebum/dust from cotton.

TABLE 10

Soil Redeposition Index Phosphorous Built Industrial Liquid Laundry Detergent

| SOIL AND FABRIC | SURFACTANTS | | |
|---|---|---|---|
| | Mobil AE + Vista LABS | Shell AE + Vista LABS | Vista LABS |
| Carbon Black/Oil | | | |
| Cotton | 99 | 99 | 97 |
| Polyester/Cotton | 99 | 101 | 99 |
| Polyester | 99 | 100 | 96 |
| Sebum/Dust | | | |
| Cotton | 97 | 95 | 98 |
| Polyester/Cotton | 98 | 100 | 98 |
| Polyester | 98 | 98 | 96 |

TABLE 11

Soil Redeposition Index Unbuilt Household Liquid Laundry Detergent

| SOIL AND FABRIC | SURFACTANTS | | |
|---|---|---|---|
| | Mobil AE | Shell AE | Vista LABS |
| Carbon Black/Oil | | | |
| Cotton | 99 | 99 | 99 |
| Polyester/Cotton | 100 | 99 | 99 |
| Polyester | 99 | 99 | 99 |
| Sebum/Dust | | | |
| Cotton | 100 | 100 | 101 |
| Polyester/Cotton | 99 | 100 | 99 |
| Polyester | 99 | 99 | 98 |

Mobil's tridecanol-ethoxylate surfactant performed like Shell Chemical's commercial AE in both an industrial and household laundry detergent. Both effectively remove particulate and sebaceous soils from cotton, cotton-polyester blend, and polyester fabrics. In most instances both are superior to LABS.

EXAMPLE 6

Biodegradation And Ecotoxicity of Tridecanol Ethoxylates

The example concerns results of marine bacteria toxicity, results of a river die-away test with 1,4-methyl-branched tridecanol-9(EO), and microbiological conversion of tridecanols to carbon dioxide.

A marine bacteria assay, a laboratory model for fish toxicity, shows toxicity for five parent AE's—1- tridecanol-9-mole-ethoxylate, 1,4-methyl branched tridecanol-9-mole-ethoxylate, 2,4-methyl branched-tridecanol-9-mole-ethoxylate, NEODOL-25-9, and EXXAL-13-9-mole ethoxylate. However, after an acclimated sewage inoculum biodegrades these AE's for 14 days, only the EXXAL-13-9-mole ethoxylate residue exhibits toxicity. The other residues are non-toxic to marine bacteria. The EXXAL 13 residues, on the other hand, show a slight increase in toxicity relative to the parent material. This correlates well with the GLPC analyses of the biodegraded materials. Only trace residues remain of 1,4-methyl branched-tridecanol-9(EO), 2,4-methyl branched-tridecanol-9(EO), 1-tridecanol-9(EO), and NEODOL-25. However, EXXAL 13 shows substantial residues. See Table 12.

TABLE 12

Tridecanol Ethoxylates
Marine Bacteria Summary

| MATERIAL | (EC$_{50}$ in PPM) | BIODEGRADED* (EC$_{50}$ in PPM) |
|---|---|---|
| 1-Tridecanol-9 (EO) | 0.59 | NT |
| NEODOL 25-9 | 1.90 | NT |
| 1,4-Tridecanol-9 (EO) | 2.91 | NT |
| 2,4-Tridecanol-9 (EO) | 3.30 | NT |
| EXXAL 13-9 (EO) | 7.97 | 7.03 |

NT = Demonstrated no toxicity to marine bacteria
*A sewage inoculum is acclimated over 3 weeks to increasing concentrations of each test material with a final acclimation concentration of 10 ppm. Each acclimated culture is then added to separate flasks containing mineral salts medium and 10 ppm of the corresponding test material. After 14 days the microorganisms are removed by centrifugation and the supernatant used in the marine bacteria assay. Values represent an EC50 (concentration resulting in 50% inhibition).

Figure 7:
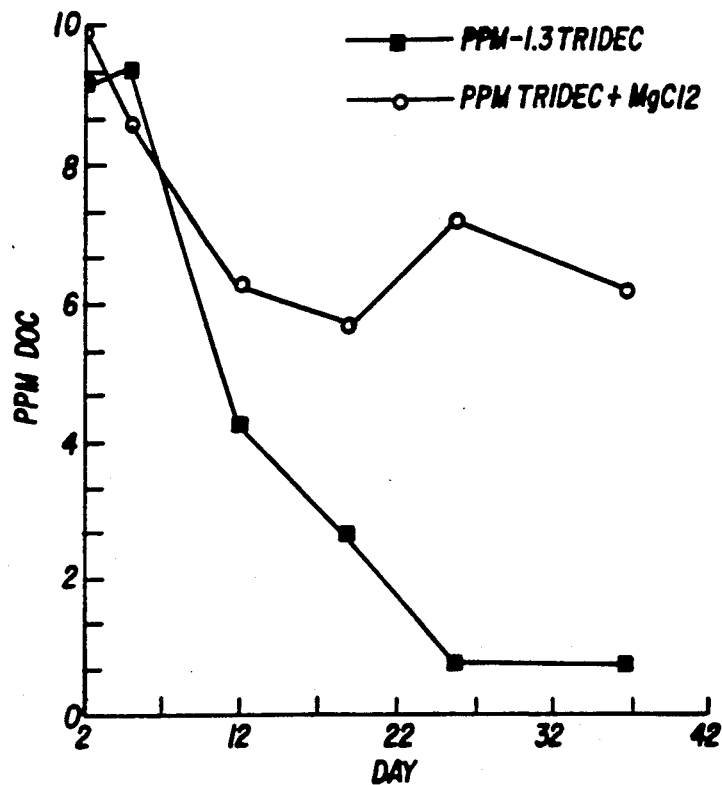
FIG. 7 shows biodegradation data.
Figure 8:
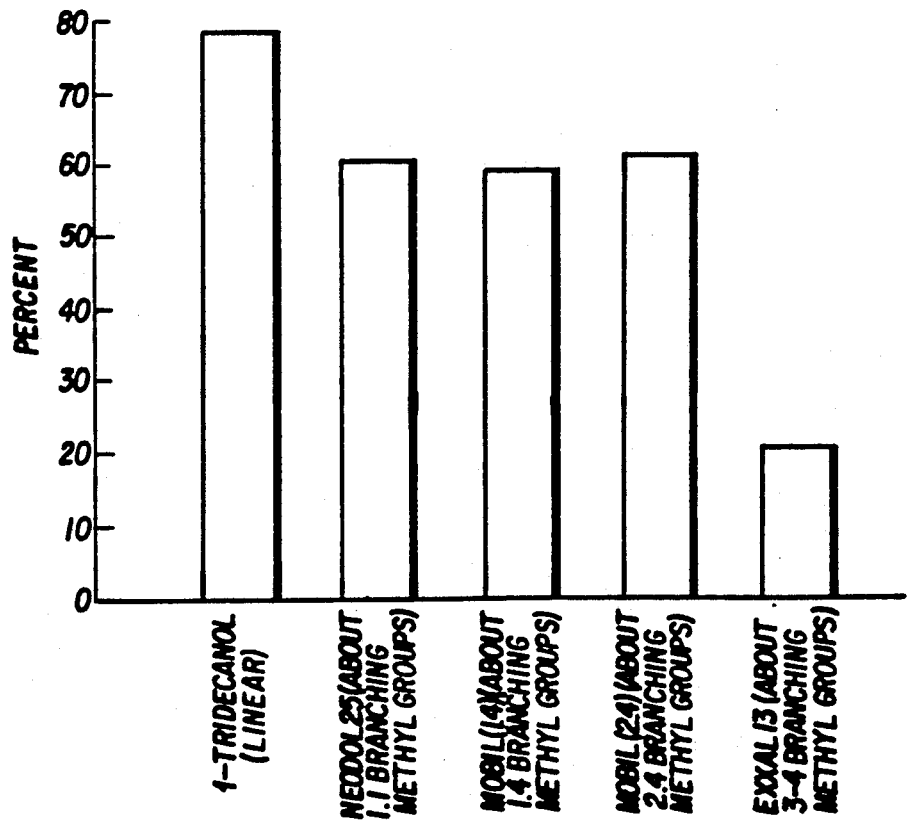
FIG. 8 shows absolute tridecanol biodegradation.

In the river die-away test, 10 ppm (carbon) of 1,4-methyl branched-tridecanol-9(EO) are added to Erlenmeyer flasks containing coarsely filtered Delaware River water. The system is kept well aerated in a rotary shaker and biodegradation activity is determined by following the disappearance of dissolved organic carbon. The results of this biodegradation together with the sterile control (mercuric chloride poisoned) are presented in FIG. 7. The data for the bioactive sample follow a classic biodegradation curve. After a lag period, the dissolved organic carbon level is reduced from 9.3 ppm to 0.8 ppm, representing a 91% reduction in dissolved organic carbon. The sterile control shows a 36% reduction in DOC during the first 12 days of the experiment but no further reduction between 12 and 37 days. The overall results indicate that in a river environment, after a reasonable acclimation period, the potential exists for rapid and substantial biodegradation of the 1,4 tridecanol-9(EO).

Table 13 gives conversion data for tridecanols going to carbon dioxide. As expected, the unbranched 1-tridecanol demonstrated the greatest extent of conversion to CO$_2$ in 28 days (76.6%). NEODOL 25, and 1,4 methyl-branched tridecanol-9(EO) and 2,4 methyl-branched tridecanol-9(EO) show no obvious differences. These proceed at the same rate and extent with 58–60% of these slightly branched alcohols being converted to CO$_2$ in 28 days. The extensively branched EXXAL 13 demonstrates a sharply lower rate and extent (20.4%) of conversion to CO$_2$. Napthalene is run as a positive control with 65% being converted to CO$_2$ in 28 days. The test uses an inoculum obtained from the Mobil Technical Center and Paulsboro refinery waste treatment plants (both in New Jersey). This inoculum is acclimated to growth on the individual alcohols over several weeks.

TABLE 13

| | DAYS INCUBATED | | | | |
|---|---|---|---|---|---|
| | 2 | 7 | 14 | 21 | 28 |
| | CUMULATIVE % BIODEGRADED TO CARBON DIOXIDE | | | | |
| 1-Tridecanol | 26.3 | 36.3 | 63.4 | 68.3 | 76.6 |
| NEODOL 25 | 27.8 | 39.1 | 50.9 | 53.8 | 59.1 |
| 1,4 Methyl Branched Tridecanol | 26.4 | 41.4 | 47.4 | 50.9 | 58.0 |
| 2,4 Methyl Branched Tridecanol | 21.5 | 40.4 | 48.0 | 56.7 | 60.1 |
| EXXAL 13 | 0 | 13.0 | 19.0 | 19.0 | 20.4 |
| NAPHTHALENE | 16.8 | 46.5 | 58.0 | 61.9 | 64.7 |

The EPA and OECD regulations generally assume that 60% of a growth substrate goes into energy generation (with the resultant complete oxidation of the material to CO$_2$) and 40% of the substrate is incorporated into cellular material. Under these circumstances any CO$_2$ conversion value of 60% or greater would indicate complete metabolism of the substrate. The values for the tridecanol-9(EO) products are at or very close to this 60% mark.

Although the invention has been described in conjunction with specific embodiments, it is evident that many alternatives and variations will be apparent to those skilled in the art in light of the foregoing description. For example, the detergents can be formulated using conventional components in conventional concentrations. A formulation surfactant, can include surfactant, C$_{12}$ sodium alkylbenzene sulfonate, triethanol amine, ethanol, potassium chloride, optical brightener, water, dye and perfume for an unbuilt heavy duty liquid detergent. A heavy duty powder detergent can include surfactant, STPP phosphate, sodium metosilicate pentahydrate, Na$_2$SO$_4$, Na$_2$CO$_3$, fumed silica and water. A hand-wash liquid can include surfactant, lauric diethanolamide, cocoamido betaine, water, brightner, perfume etc. Other formulations can be prepared by those skilled in the art. Accordingly, the invention is intended to embrace all of the alternatives and variations that fall within the intended spirit and scope of the appended claims.

We claim:

1. A process for the production of biodegradable surfactant comprising:
   a) contacting C$_3$, C$_4$ olefins, or mixtures thereof, with ZSM-23 catalyst under oligomerization conditions to form oligomers having the formula (C$_3$)$_x$, (C$_4$)$_x$, or mixtures thereof, where x has the value of 1 to 10, said oligomers having an average of 0.8 to 2.0 methyl branches per 12 carbon atoms;
   b) contacting step (a) oligomers with hydroformylating catalyst comprising tributyl phosphine modified cobalt carbonyl under hydroformylating conditions comprising temperature between 140° C. and 180° C. and pressure between 200 psig and 1000 psig to form a saturated alcohol containing an average of not more than 2.5 methyl branches per 12 carbon atoms;
   c) reacting step (b) saturated alcohol with ethylene oxide, or derivative thereof, under ethoxylating conditions comprising temperature below 150° C. in contact with ethoxylating catalyst comprising potassium alcoholate; and
   d) recovering a nonionic branched biodegradable surfactant containing an average of about 9 ethylene oxide recurring units.

2. The process according to claim 1, wherein x equals 4.

3. The process according to claim 1, wherein the saturated alcohol is a $C_{10}$-$C_{16}$ alcohol.

4. The process according to claim 3, wherein the saturated alcohol is tridecanol.

5. A nonionic $C_{10}$-$C_{16}$ alcohol ethoxylate produced according to the process of claim 1.

6. An alcohol ethoxylate according to claim 5, wherein the ethoxylate is a $C_{13}$ alcohol ethoxylate.

7. A biodegradable surfactant comprising a nonionic $C_{10}$-$C_{16}$ alcohol ethoxylate produced according to the process of claim 1.

8. A surfactant according to claim 7, comprising a nonionic $C_{13}$ alcohol ethoxylate.

* * * * *